(12) United States Patent
Uchida et al.

(10) Patent No.: US 12,263,197 B2
(45) Date of Patent: Apr. 1, 2025

(54) ONCOLYTIC VIRUS FOR CANCER THERAPY

(71) Applicant: The University of Tokyo, Tokyo (JP)

(72) Inventors: Hiroaki Uchida, Tokyo (JP); Hideaki Tahara, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 956 days.

(21) Appl. No.: 17/288,227

(22) PCT Filed: Oct. 30, 2019

(86) PCT No.: PCT/JP2019/042526
§ 371 (c)(1),
(2) Date: Apr. 23, 2021

(87) PCT Pub. No.: WO2020/090871
PCT Pub. Date: May 7, 2020

(65) Prior Publication Data
US 2021/0386807 A1    Dec. 16, 2021

(30) Foreign Application Priority Data

Oct. 30, 2018 (JP) ................................. 2018-203553

(51) Int. Cl.
*A61K 35/763* (2015.01)
*A61P 35/00* (2006.01)

(52) U.S. Cl.
CPC ............ *A61K 35/763* (2013.01); *A61P 35/00* (2018.01)

(58) Field of Classification Search
None
See application file for complete search history.

(56) References Cited

FOREIGN PATENT DOCUMENTS

JP        2005-521398         7/2005

OTHER PUBLICATIONS

Okubo, et al. J Virol. Nov. 28, 2016;90(24):11096-11105. doi: 10.1128/JVI.01456-16. PMID: 27707922 (Year: 2016).*
Shibata, et al. Gene Ther. Jun. 2016;23(6):479-88. doi: 10.1038/gt. 2016.17. Epub Feb. 23, 2016. PMID: 26905369 (Year: 2016).*
Okubo, Yu et al., "Syncytial Mutations Do Not Impair the Specificity of Entry and Spread of a Glycoprotein D Receptor-Retargeted Herpes Simplex Virus", Journal of Virology, Dec. 2016, vol. 90, No. 24, pp. 11096-11105.
Suzukki ,Takuma et al., "Development of oncolytic virus therapy using herpes simplex virus which inserted a cancer-targeting single-chain antibody into envelope glycoprotein gD", The 61th Annual Meeting of the Japanese Society for Virology, vol. 61, p. 27, (Mar. 4, 2016), 2013, with a partial English-Language translation.
Andtbacka, Robert H.I. et al., "Talimogene Laherparepvec Improves Durable Response Rate in Patients With Advanced Melanoma", Journal of Clinical Oncology, Sep. 1, 2015, vol. 33, No. 25, pp. 1-13.
Montgomery, Rebecca I. et al., "Herpes Simplex Virus-1 Entry into Cells Mediated by a Novel Member of the TNF/NGF Receptor Family", Cell, Nov. 1, 1996, vol. 87, pp. 427-436.
Geraghty, Robert J. et al., "Entry of Alphaherpesviruses Mediated by Poliovirus Receptor-Related Protein 1 and Poliovirus Receptor", Science, Jun. 5, 1998, vol. 280, pp. 1618-1620.
Shukla, Deepak et al., "A Novel Role for 3-O-Sulfated Heparan Sulfate in Herpes Simplex Virus 1 Entry", Cell, Oct. 1, 1999, vol. 99, pp. 13-22.
Shibata, T. et al., "Development of an oncolytic HSV vector fully retargeted specifically to cellular EpCAM for virus entry and cell-to-cell spread", Gene Therapy, 2016, vol. 23, pp. 479-488.
Uchida, Hiroaki et al., "Effective Treatment of an Orthotopic Xenograft Model of Human Glioblastoma Using an EGFR-retargeted Oncolytic Herpes Simplex Virus", Molecular Therapy, Mar. 2013, vol. 21, No. 3, pp. 561-569.
Uchida, Hiroaki et al., "A Double Mutation in Glycoprotein gB Compensates for Ineffective gD-Dependent Initiation of Herpes Simplex Virus Type 1 Infection", Journal of Virology, Dec. 2010, vol. 84, No. 23, pp. 12200-12209.
Ejercito, Pilarica M. et al., "Characterization of Herpes Simplex Virus Strains Differing in their Effects on Social Behaviour of Infected Cells", J. gen. Virol., 1968, vol. 2, pp. 357-364.
Liu, BL. et al., "ICP34.5 deleted herpes simplex virus with enhanced oncolytic, immune stimulating, and anti-tumour properties", Gene Therapy, 2003, vol. 10, pp. 292-303.
Todo, Tomoki et al., "Oncolytic herpes simplex virus vector with enhanced MHC class I presentation and tumor cell killing", PNAS, May 22, 2001, vol. 98, No. 11, pp. 6396-6401.
International Search Report issued Feb. 4, 2020 in International (PCT) Application No. PCT/JP2019/042526, with English-language translation.
Extended European Search Report issued Jul. 29, 2022 in corresponding European Patent Application No. 19880535.0.
Laura Menotti et al., "HSV as a Platform for the Generation of Retargeted, Armed, and Reporter-Expressing Oncolytic Viruses", Viruses, vol. 10, No. 352, pp. 1-29, 2018.
Maria Ekblad et al., "Molecular basis for resistance of herps simplex virus type 1 mutants to the sulfated oligosaccharide inhibitor PI-88", Virology, vol. 367, pp. 244-252, 2007.

(Continued)

*Primary Examiner* — Benjamin P Blumel
*Assistant Examiner* — Jeffrey Mark Sifford
(74) *Attorney, Agent, or Firm* — GREENBLUM & BERNSTEIN, P.L.C.

(57) ABSTRACT

It is an object of the present invention to develop a virus preparation comprising an oncolytic HSV having, in vivo, more effective cancer cell-killing activity than the antitumor effects of existing oncolytic HSVs. Specifically, the present invention relates to a virus preparation for the treatment of a cancer, comprising an HSV (herpes simplex virus) having a receptor-retargeted gD mutation and at least one membrane fusion activity-promoting region on the genome, and a method for treating cancer using the aforementioned virus preparation.

18 Claims, 13 Drawing Sheets
Specification includes a Sequence Listing.

(56) References Cited

OTHER PUBLICATIONS

Tracy Terry-Allison et al., "HveA (Herpesvirus Entry Mediator A), a Coreceptor for Herpes Simplex Virus Entry, also Participates in Virus-Induced Cell Fusion", Journal of Virology, vol. 72, No. 7, pp. 5802-5810, XP-002923344, 1998.
Office Action issued Sep. 5, 2023 in Japanese patent application No. 2020-553970, and English translation thereof.
Office Action dated Jan. 30, 2024 issued in Japanese patent application No. 2020-553970, with English translation thereof.

* cited by examiner

[Figure 1]
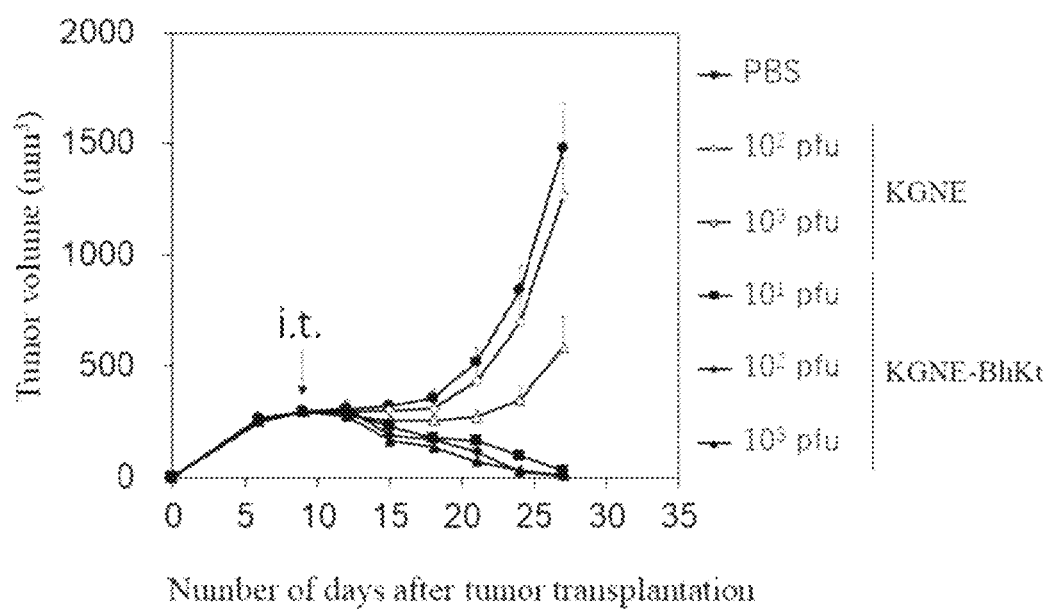

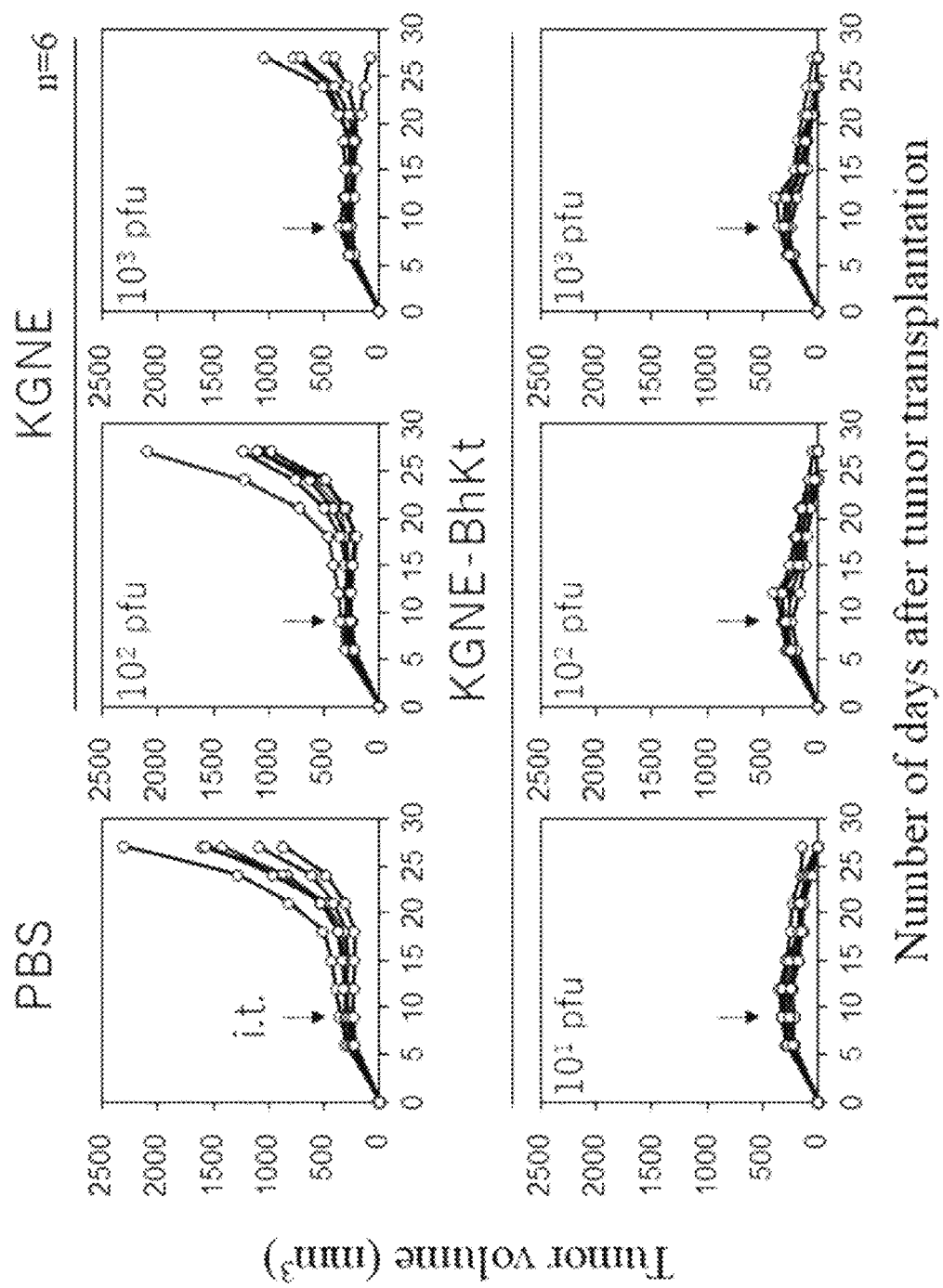
[Figure 2]

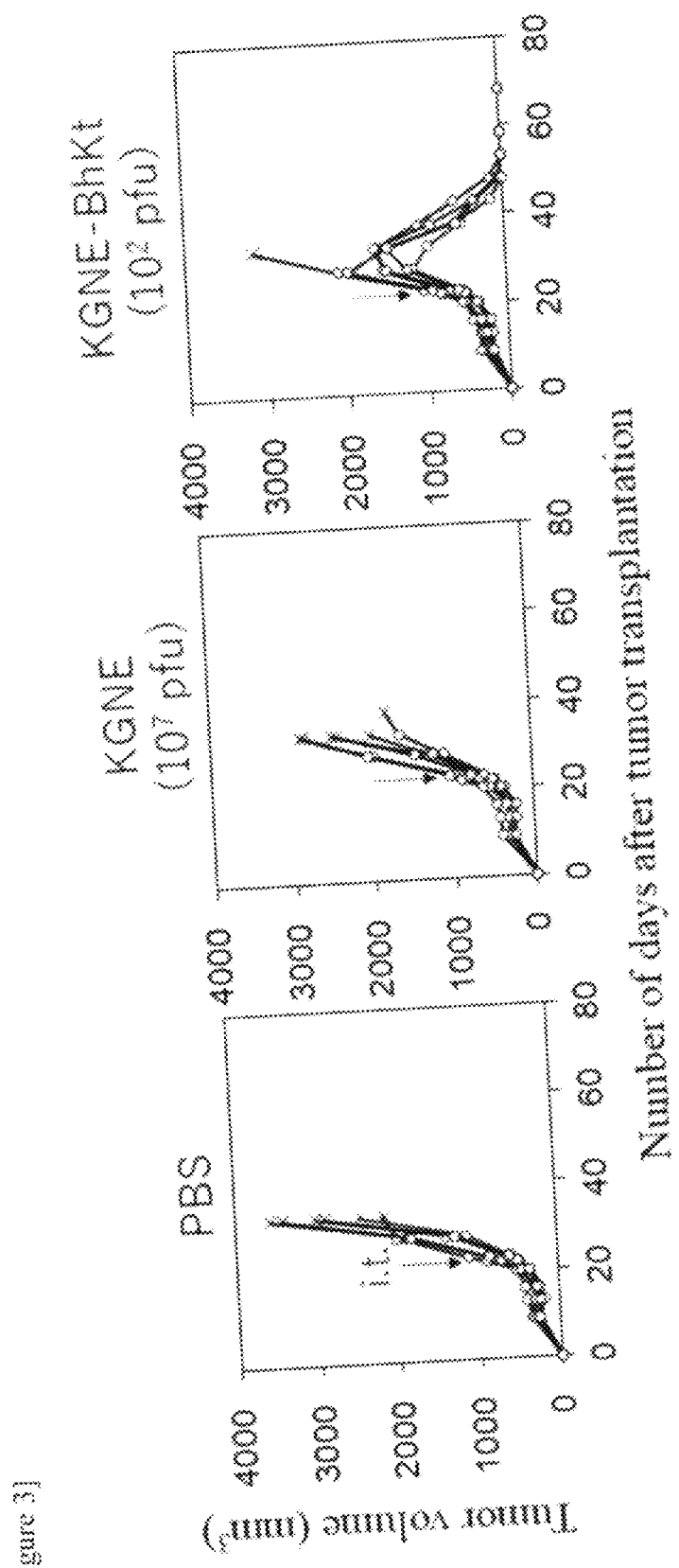
[Figure 3]

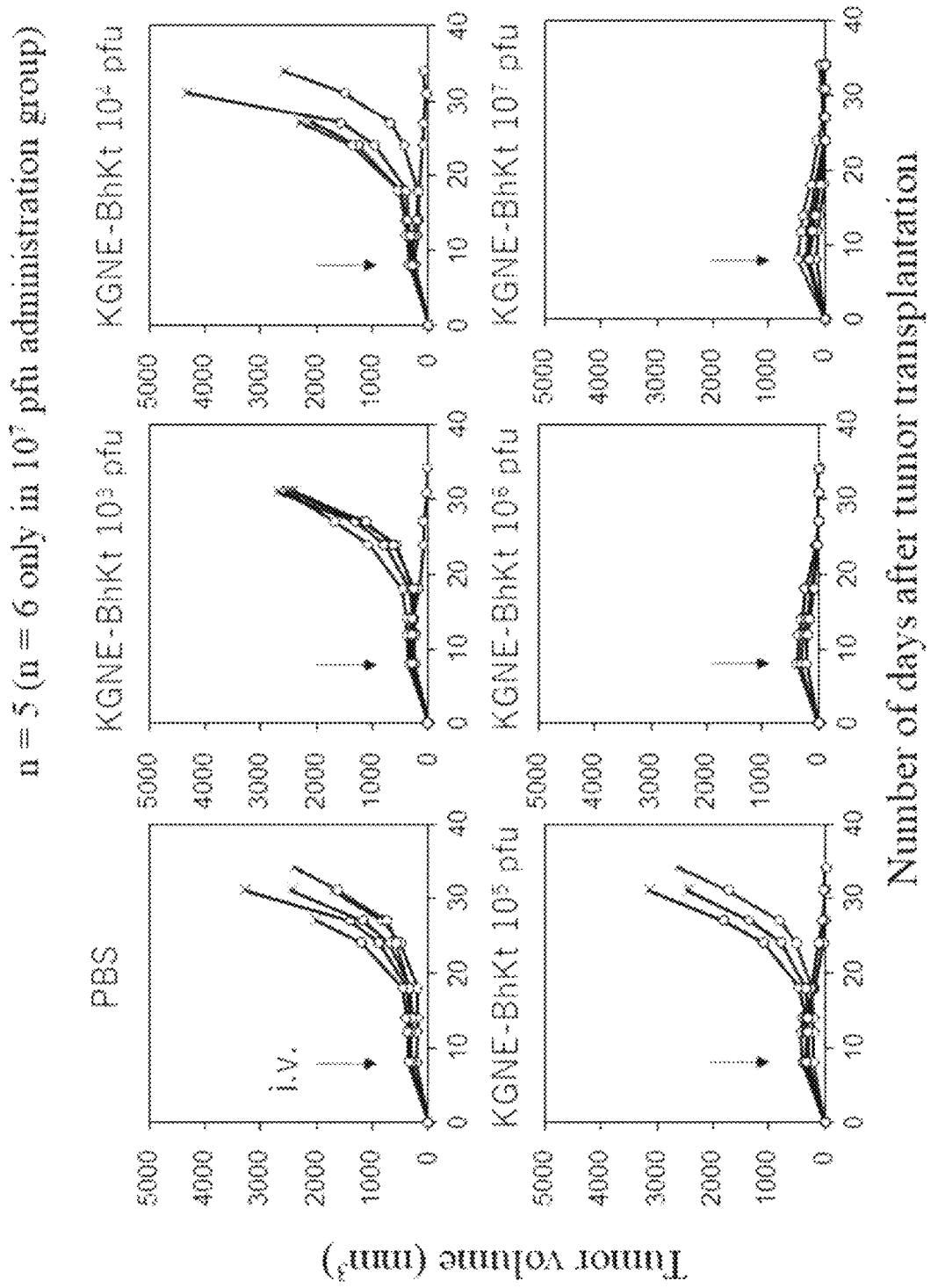
[Figure 4]

[Figure 5]
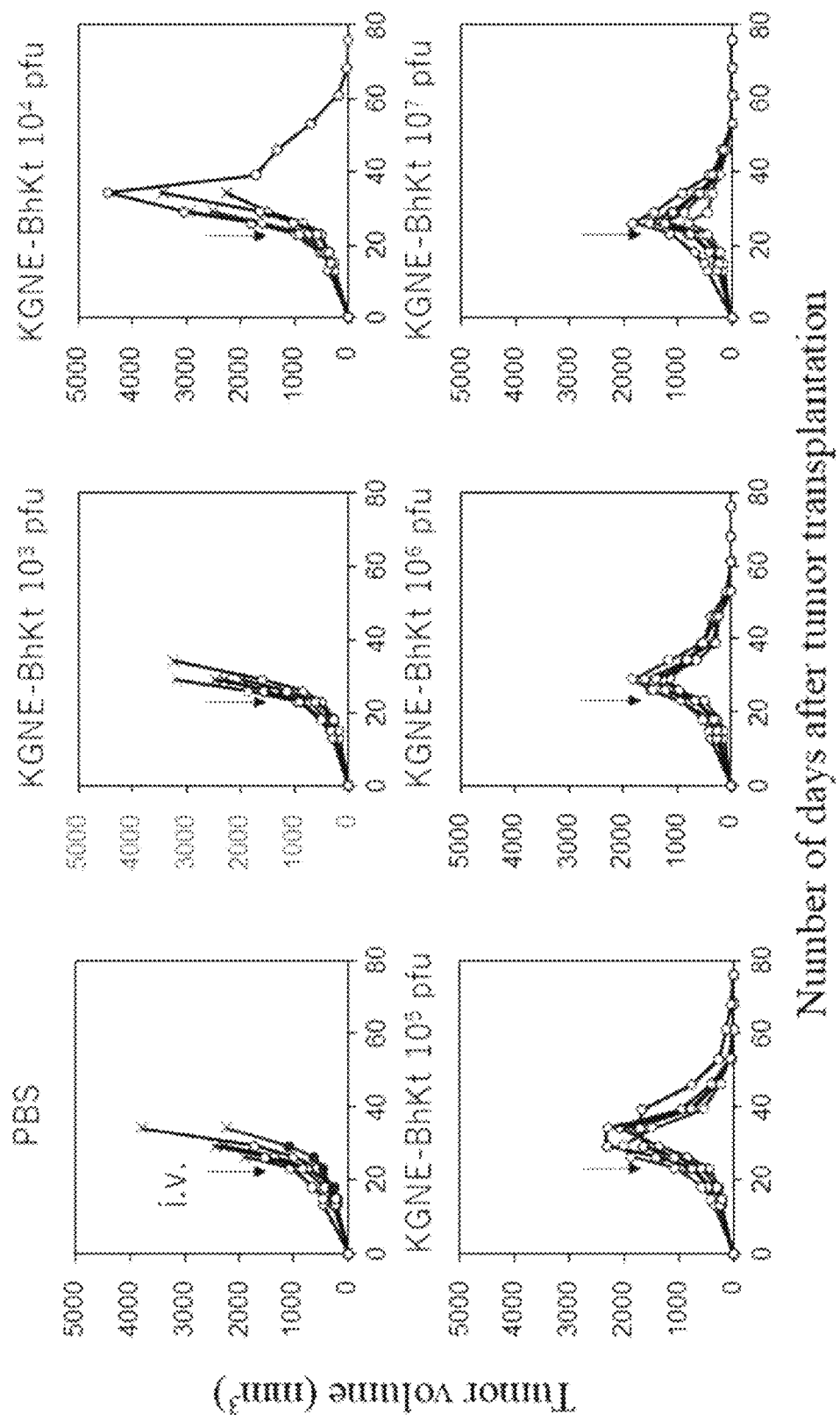

[Figure 6]
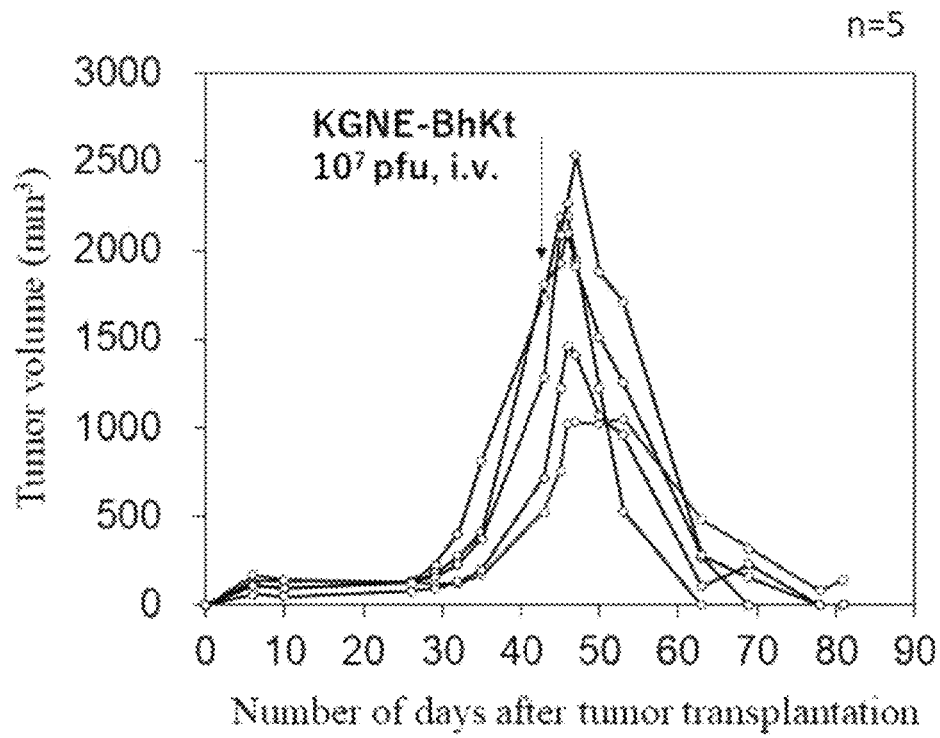
[Figure 7]
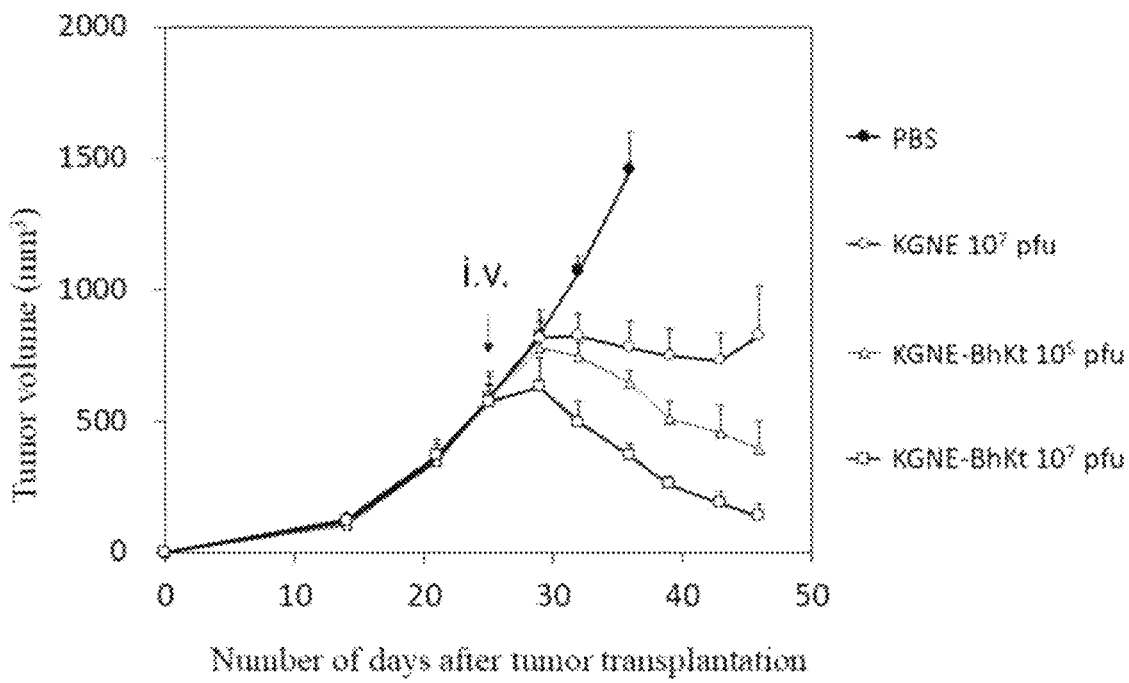

[Figure 8]
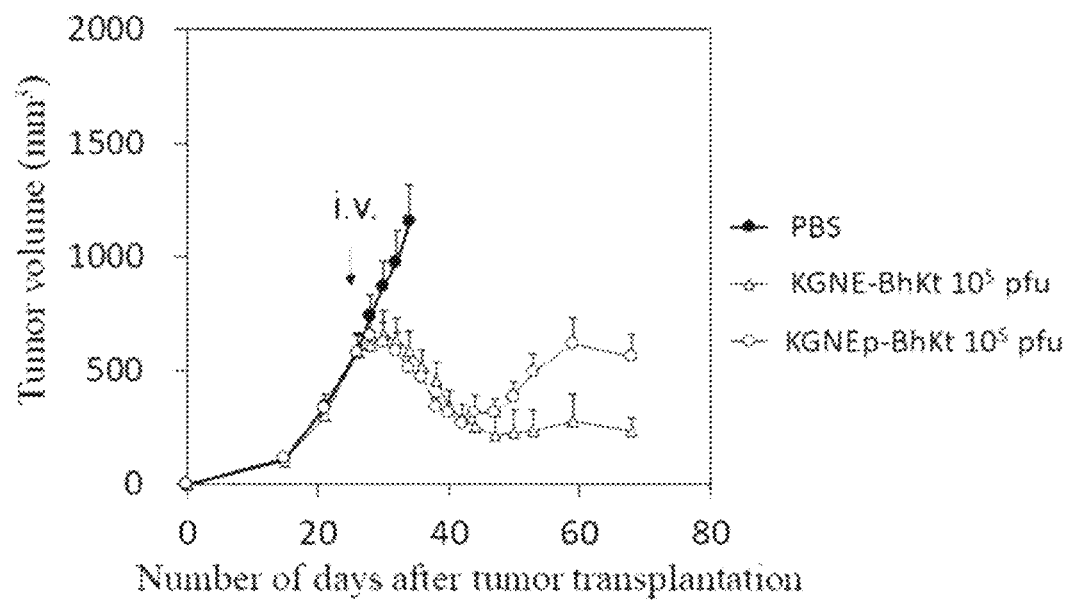
[Figure 9]
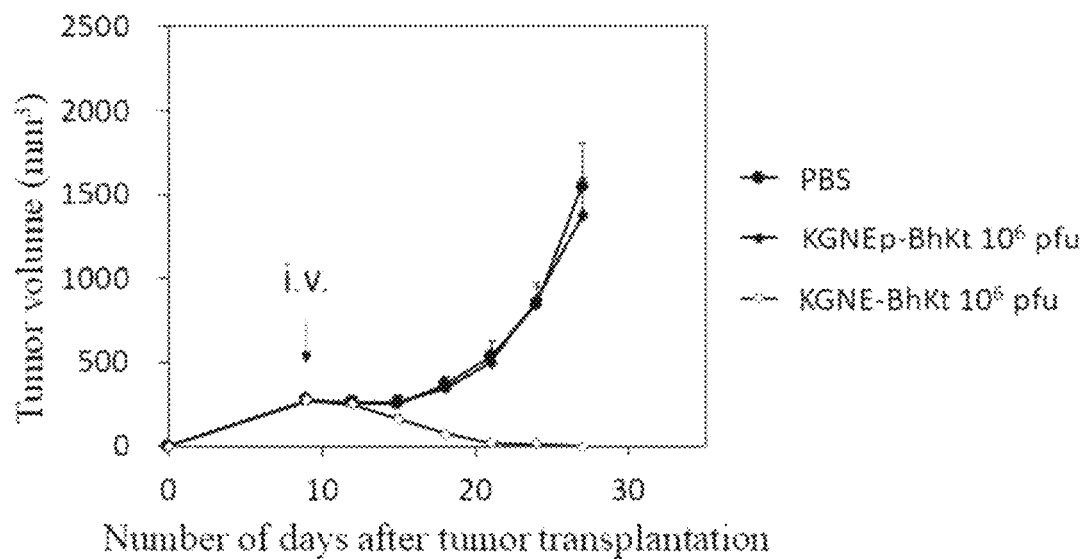

[Figure 10]
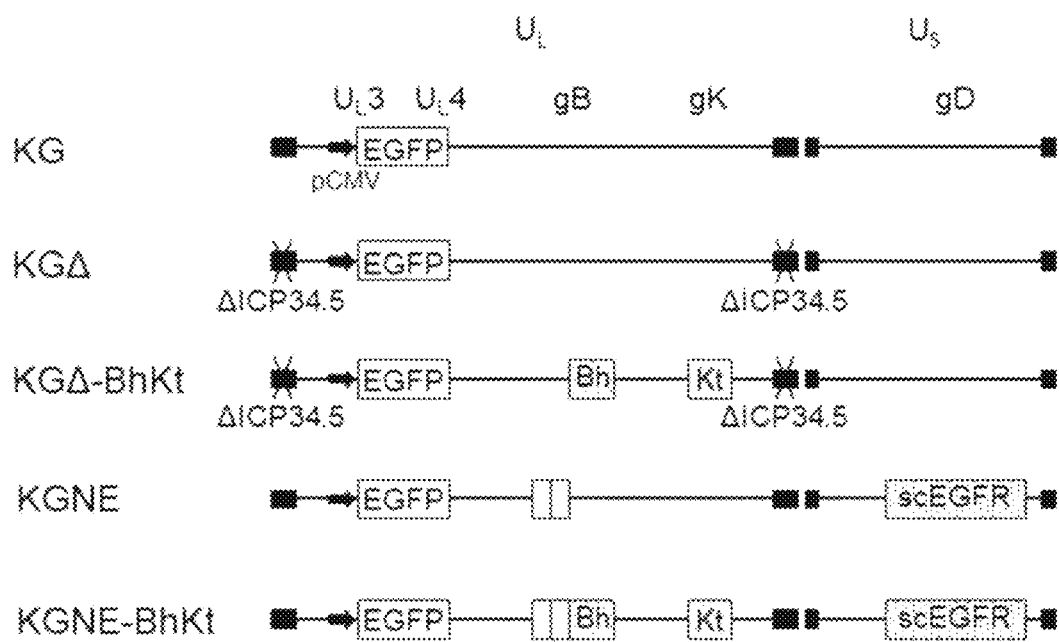

[Figure 11]
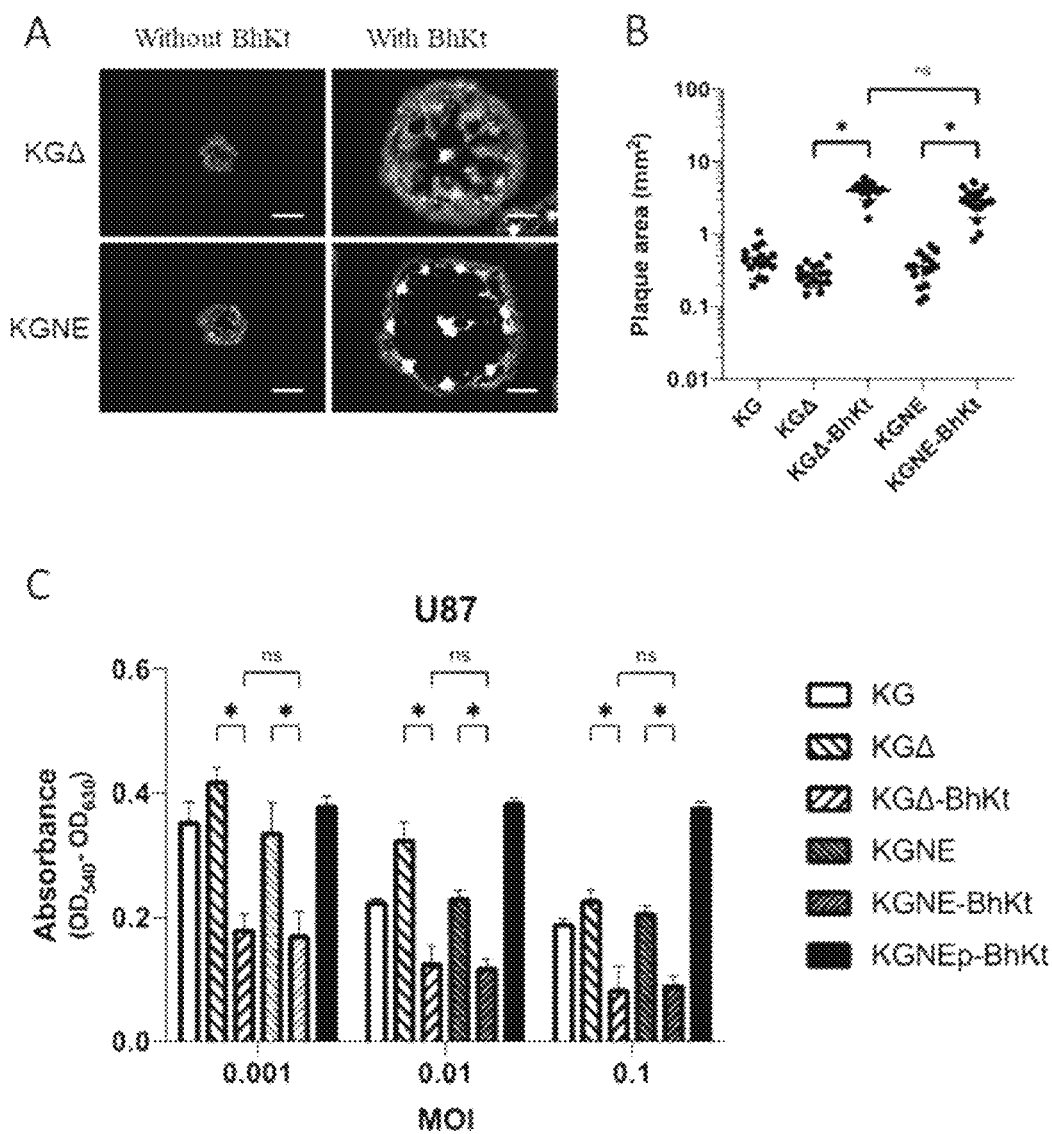

[Figure 12]
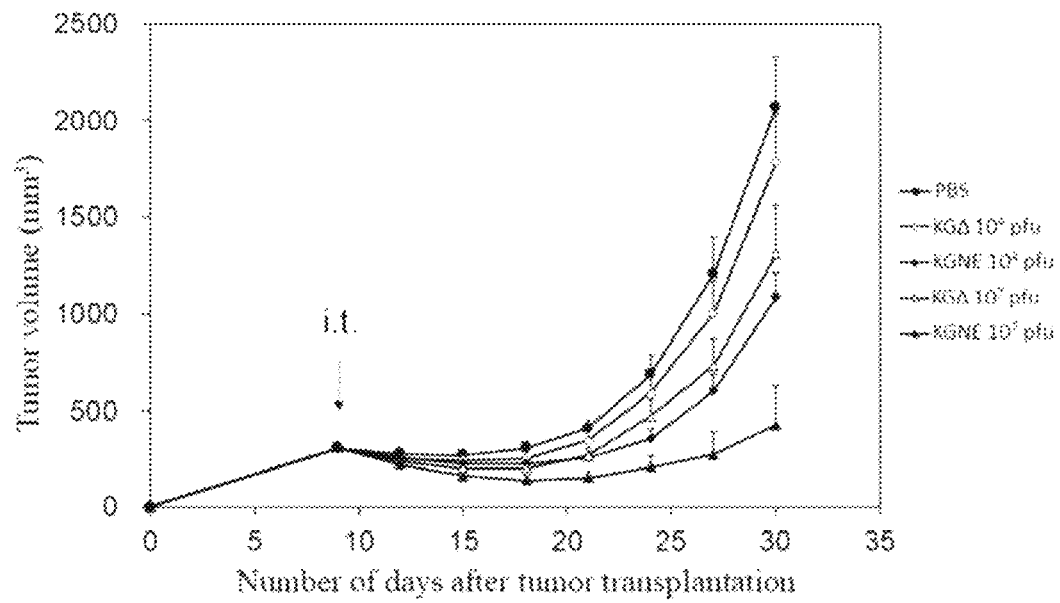
[Figure 13]
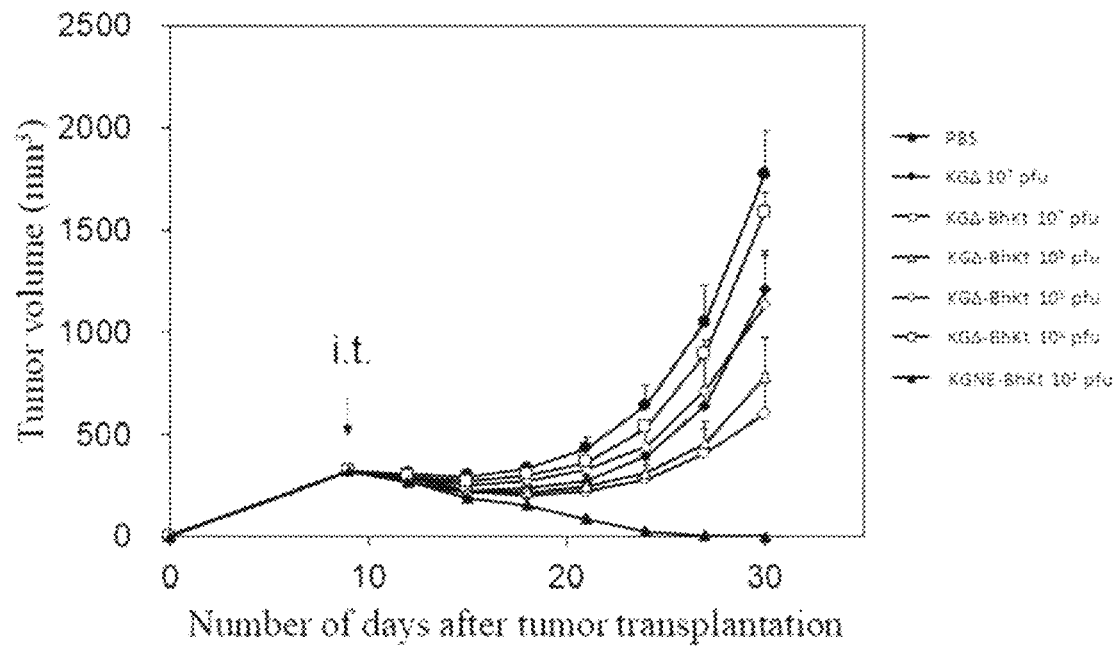

[Figure 14]
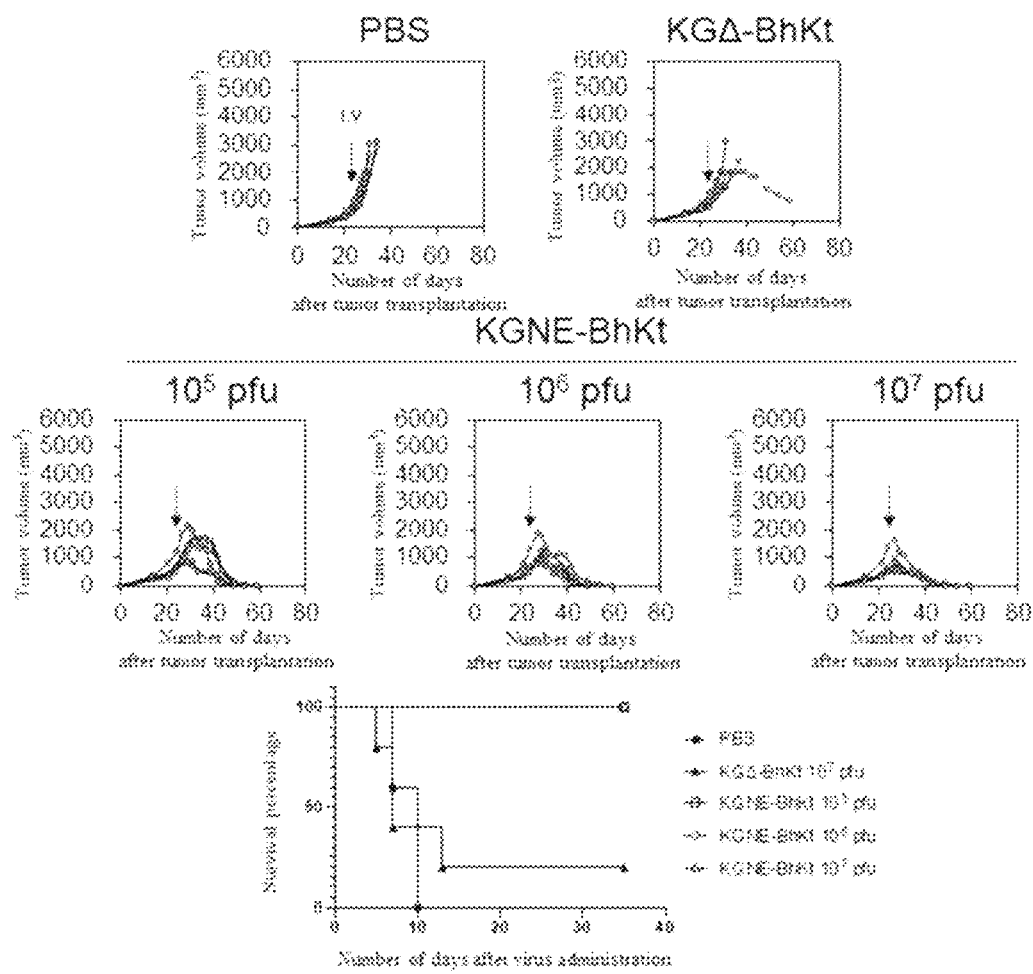

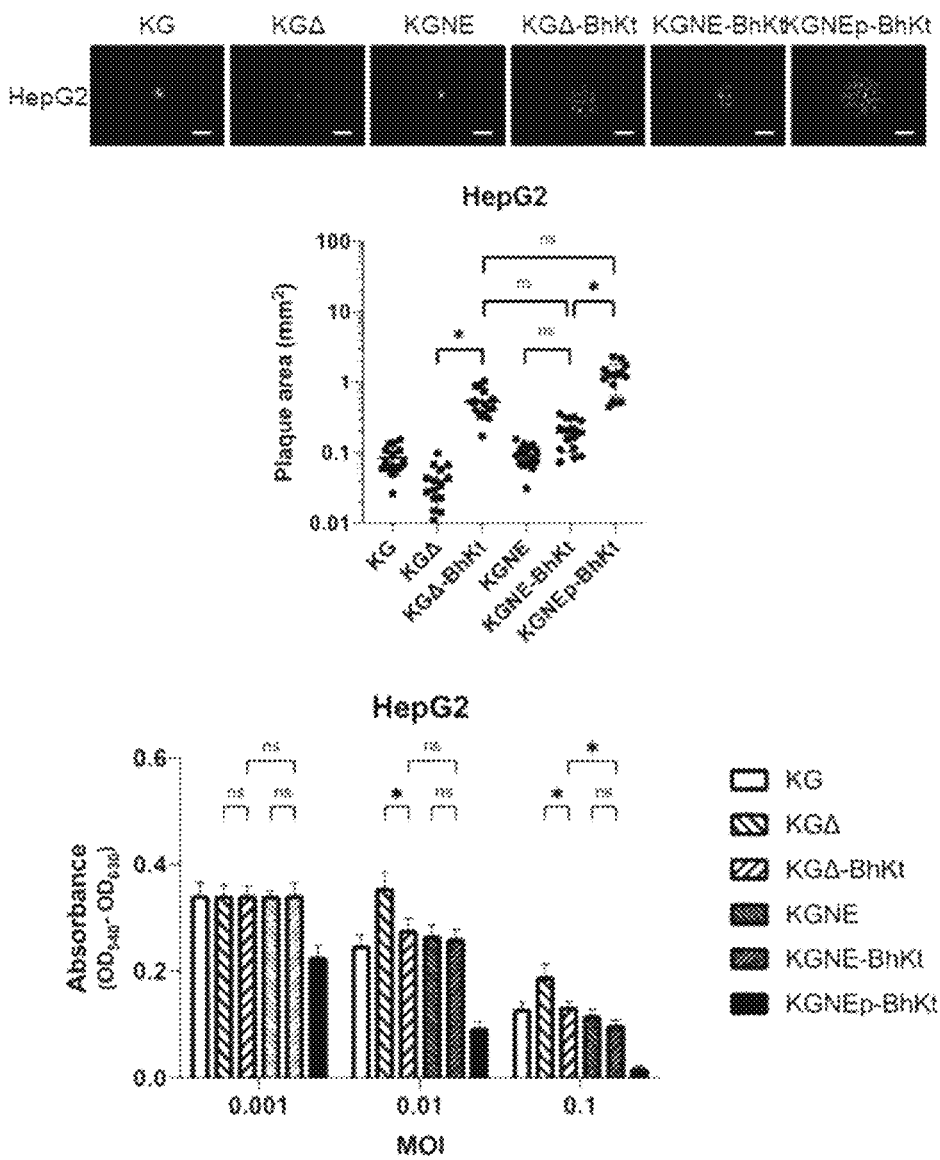
[Figure 15]

[Figure 16]
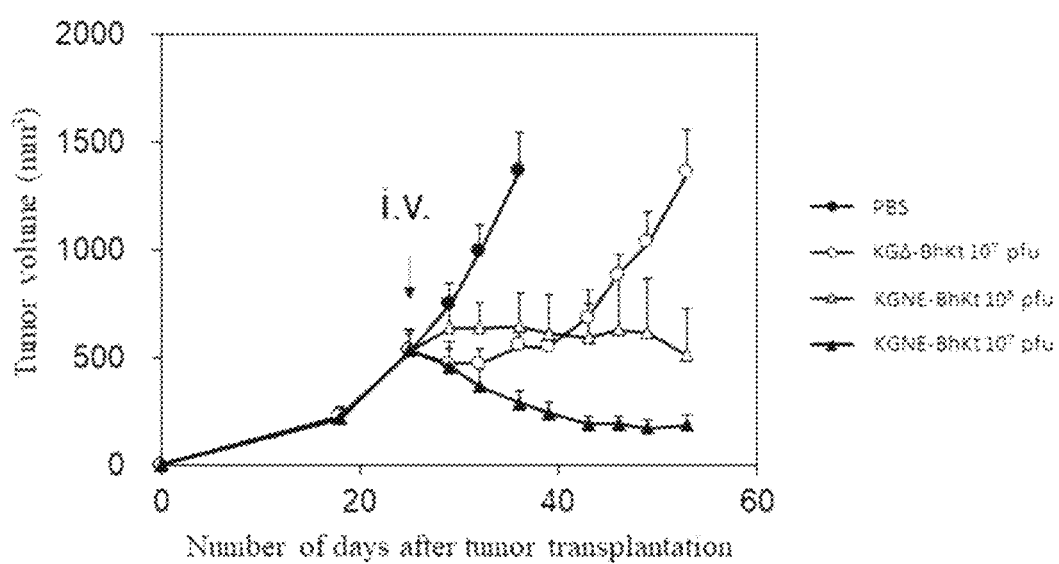

ONCOLYTIC VIRUS FOR CANCER THERAPY

TECHNICAL FIELD

The present invention relates to a virus preparation for cancer therapy, comprising an oncolytic virus, and a method for treating cancer using the oncolytic virus.

BACKGROUND ART

As a novel therapeutic method for malignant tumors, oncolytic virotherapy using herpes simplex virus (HSV) has been considered to be a promising method, and clinical trials have been promoted in a wide variety of countries including Japan, so far.

In 2015, T-VEC (talimogene laherparepvec), a genetically modified HSV preparation developed by Amgen, has been approved as a pharmaceutical product for the first time in Europe and the United States. In association with this, the present research field has attracted a further great attention. However, oncolytic viruses used in the previous clinical trials have been problematic in that the oncolytic viruses once enter not only cancer cells but also normal cells. As such, there has been a dilemma, in which in order to avoid the damage of normal cells after entry of a virus, the proliferating ability of the virus must be attenuated, and this may lead to a decrease in the oncolytic ability. In addition, in order to secure the amount of a virus necessary for oncolysis at a tumoral location, the virus must be directly administered into the tumor, and this has been a great obstacle in the treatment of advanced cancer having distant metastasis (in fact, in clinical trials regarding the effects of T-VEC on malignant melanoma, a significant prolongation in survival period was not observed in a patient group having distant metastasis to the lung or liver (Non Patent Literature 1)).

Regarding this problem, if an ideal targeted virus that can enter only cancer cells were practicalized, it would become possible to develop a treatment strategy that makes the most of the original oncolytic ability, without attenuating the proliferating ability of the virus. Moreover, by intravenously administering such a virus, it would also become possible to treat cancer cases involving systemic metastasis.

Entry of an HSV into a cell is initiated by the binding of gD (glycoprotein D) as an envelope glycoprotein of the HSV with HVEM (herpesvirus entry mediator) and nectin-1, or 3-O-sulfated heparan sulfate (3-OS-HS) as a receptor of the gD that exists on the surface of the cell (Non Patent Literature 2 to Non Patent Literature 4). The present inventors have focused on this initial entry process, and have studied a method of allowing the HSV to specifically enter a tumor cell as a target. As a result, the present inventors have succeeded in modifying the receptor usage in an HSV infection (Non Patent Literature 5 to Non Patent Literature 7). Specifically, the present inventors have made impossible for the gD playing a role in the invasion entry of the HSV into cells to bind to the original receptor, and have then fused scFv (single-chain antibody) reacting against various tumor-associated antigens such as EGFR (epidermal growth factor receptor), CEA (carcinoembryonic antigen) and EpCAM (epithelial cell adhesion molecule) with the modified gD, followed by the expression thereof, so that the inventors have succeeded in constructing a targeted HSV efficiently entering only the target cells.

After entry of HSV into a cell, the HSV spreads the infection range as a result of cell-to-cell spread. This cell-to-cell spread progresses as a result of the release of progeny virus particles between infected cells and adjacent uninfected cells. The cells infected due to cell-to-cell spread have a round shape and aggregate with one another, but the fusion of the cell membranes hardly occurs (Non Patent Literature 8).

The present inventors have developed a method of providing a strong cell-killing effect, the method comprising introducing a plurality of syn mutations (syncytial mutations) for promoting the membrane fusion activity of the HSV into cells, so as to efficiently achieve the cell-to-cell spread of the HSV that has undergone target cell-specific entry (Non Patent Literature 9). That is, a virus was produced by incorporating either one or both of the syn mutations of gB (glycoprotein B) and gK (glycoprotein K) into a targeted HSV. As a result, the virus produced by incorporation of the two syn mutations formed a plaque consisting of extremely large multinucleated giant cells in a human pancreatic cancer cell line, in which only a small plaque had been formed by a parent virus strain (virus not having such syn mutations), and the produced virus demonstrated a strong cancer cell-killing activity. Moreover, it was not observed that infected target cancer cells were fused with non-target cells that were adjacent to the target cancer cells, and that the infection was thus spread. From these results, it was elucidated that a syn mutation-introduced targeted HSV has excellent effects, by which the cancer cell-killing activity thereof is enhanced, while maintaining its high cancer specificity.

It became clear that the aforementioned HSV subjected to receptor-retargeting modification and membrane fusion-promoting mutation (Non Patent Literature 9) exhibits a strong cancer cell-killing activity on cultured cells (in vitro).

However, the level of antitumor effect exhibited by the thus modified HSV in a living body (in vivo), compared with an HSV subjected to only the receptor-retargeting modification, or compared with the preceding oncolytic virus that targets a cancer at a stage of HSV replication in cells and the preceding oncolytic virus further subjected to the membrane fusion-promoting mutation, is still unknown at the moment.

CITATION LIST

Non Patent Literature

Non Patent Literature 1: Andtbacka et al., J Clin Oncol. 33: 2780-2788, 2015
Non Patent Literature 2: Montgomery et al., Cell 87: 427-436, 1996
Non Patent Literature 3: Geraghty et al., Science 280: 1618-1620, 1998
Non Patent Literature 4: Shukla et al., Cell 99: 13-22, 1999
Non Patent Literature 5: Shibata et al., Gene Ther. 23: 479-488, 2016
Non Patent Literature 6: Uchida et al., Mol Ther. 21: 561-569, 2013
Non Patent Literature 7: Uchida et al., J Virol. 84: 12200-12209, 2010
Non Patent Literature 8: Ejercito et al., J Gen Virol. 2: 357-364, 1968
Non Patent Literature 9: Okubo et al., J Virol. 90: 11096-11105, 2016
Non Patent Literature 10: Liu et al., Gene Ther. 10: 292-303, 2003

Non Patent Literature 11: Todo et al., Proc Natl Acad Sci USA. 98: 6396-6401, 2001

SUMMARY OF INVENTION

Technical Problem

Under the aforementioned circumstance, it is an object of the present invention to develop a virus preparation comprising an oncolytic HSV having a higher cancer cell-killing activity than existing oncolytic HSVs in vivo.

Solution to Problem

The present inventors introduced a mutation into the gD gene of an HSV to modify a receptor (hereinafter, this HSV is also referred to as "RR-oHSV (receptor-retargeted oncolytic HSV)"), and then studied the antitumor effect of syn mutation-introduced RR-oHSV (hereinafter, also referred to as "RR-oHSV-syn"), using subcutaneous tumor xenograft mouse models. As a result, the following points were revealed.

First, the aforementioned receptor-retargeted gD mutation- and syn mutation-introduced HSV was administered once into the tumor (volume: approximately 300 mm$^3$) of subcutaneous tumor xenograft mouse models (mice into which human glioma U87 cells had been transplanted). As a result, an extremely small amount ($10^1$ pfu) of the administered HSV exhibited a strong antitumor effect (see FIG. 1). With regard to the results of similar experiments conducted by other research groups, it has been reported that an antitumor effect was confirmed by intratumoral administration of 5×10$^6$ pfu of HSV into a tumor with a volume of approximately 32 mm$^3$ (see FIG. 4 of Non Patent Literature 10, etc.), and that an antitumor effect was confirmed by intratumoral administration of 1×10$^6$ pfu of HSV into a tumor with a volume of approximately 108 mm$^3$ (see FIG. 6 of Non Patent Literature 11, etc.). In these experiments conducted by other groups, although the volume of a tumor was smaller than the volume of a tumor in the experiment conducted by the present inventors, the dose applied to obtain an antitumor effect was significantly large ($10^6$ pfu order), and further, such an antitumor effect was confirmed after intratumoral administration had been performed multiple times (twice or three times). Accordingly, it can be evaluated that an oncolytic HSV having both the receptor-retargeted gD mutation and the syn mutation exhibits a stronger antitumor effect in an extremely small amount of the virus, compared with the preceding oncolytic HSVs. In particular, the in vivo antitumor effect of an HSV, on which the syn mutation, as well as the receptor-retargeted gD mutation, had been performed, was a significant effect that was unpredictable from the in vitro experimental results. That is to say, in in vitro experiments, the cancer cell-killing effect of an oncolytic HSV having both the receptor-retargeted gD mutation and the syn mutation was merely several hundred times the cancer cell-killing effect of an oncolytic HSV having only the receptor-retargeted gD mutation, in terms of the median lethal dose (LD$_{50}$). In contrast, in in vivo experiments, the cancer cell-killing effect of the oncolytic HSV having both the receptor-retargeted gD mutation and the syn mutation was 100,000 times or more the cancer cell-killing effect of an oncolytic HSV having only the receptor-retargeted gD mutation, which greatly exceeded expectations.

Furthermore, the present inventors made a comparison between a conditionally replicating oncolytic HSV (hereinafter referred to as "CR-oHSV") having no mutations on the gD gene but having a mutation to attenuate the replication thereof in normal cells (for example, a deletion of ICP34.5, etc.) and also having a syn mutation (hereinafter also referred to as "CR-oHSV-syn") and the above-described RR-oHSV-syn of the present invention, in terms of antitumor effect. In vitro, RR-oHSV-syn was equivalent to CR-oHSV-syn, in terms of cancer cell-killing ability. However, in vivo, it was confirmed that the antitumor effect of RR-oHSV-syn was at least approximately 1,000,000 times higher than the antitumor effect of CR-oHSV-syn by intratumoral administration, and that the antitumor effect of RR-oHSV-syn was at least approximately 100 times higher than the antitumor effect of CR-oHSV-syn even by systemic administration.

The above results demonstrate that the antitumor effect of the oncolytic HSV having both the receptor-retargeted gD mutation and the syn mutation (RR-oHSV-syn) developed by the present inventors is more excellent in vivo than the antitumor effects of oncolytic HSVs reported by other groups, and that such excellent antitumor effect of the present oncolytic HSV is unpredictable by a person skilled in the art.

The present invention has been completed based on the aforementioned findings.

Specifically, the present invention includes the following (1) to (9).

(1) A virus preparation for the treatment of a cancer, comprising an HSV (herpes simplex virus) having a receptor-retargeted gD mutation and at least one membrane fusion activity-promoting region on the genome.

(2) The virus preparation according to the above (1), which is characterized in that the membrane fusion activity-promoting region is a region having a syn mutation or a membrane fusion-promoting foreign gene region.

(3) The virus preparation according to the above (1) or (2), which is characterized in that, among the receptor-retargeted gD mutations, the mutation to delete binding ability to nectin-1 is a deletion of all of the amino acids at positions 6 to 38 of SEQ ID NO: 1, a deletion of all of the amino acids at positions 61 to 218 of SEQ ID NO: 1, a mutation of the amino acids at positions 3 and 38 of SEQ ID NO: 1, and/or a mutation of the amino acids at positions 222 and 223 of SEQ ID NO: 1.

(4) The virus preparation according to the above (3), which is characterized in that the amino acid mutation at position 3 of SEQ ID NO: 1 is a deletion or a substitution with cysteine, the amino acid mutation at position 38 of SEQ ID NO: 1 is a substitution with cysteine, the amino acid mutation at position 222 of SEQ ID NO: 1 is a substitution with asparagine, and the amino acid mutation at position 223 of SEQ ID NO: 1 is a substitution with isoleucine.

(5) The virus preparation according to the above (1) or (2), which is characterized in that, among the receptor-retargeted gD mutations, the mutation to delete binding ability to HVEM and 3-OS-HS is a deletion of all or a part of the amino acids at positions 2 to 38 of SEQ ID NO: 1, a deletion of all of the amino acids at positions 61 to 218 of SEQ ID NO: 1, an amino acid mutation at position 27 of SEQ ID NO: 1, an amino acid mutation at position 29 of SEQ ID NO: 1, and/or an amino acid mutation at position 30 of SEQ ID NO: 1.

(6) The virus preparation according to the above (5), which is characterized in that: the deletion of a part of the amino acids at positions 2 to 38 of SEQ ID NO: 1 is any one of a deletion of the amino acids at positions 2 to 24, a deletion of the amino acids at positions 7 to 11, a deletion of the amino acids at positions 7 to 32, or a deletion of the amino acids at positions 6 to 38; the amino acid mutation at position 27 is a substitution with alanine, proline or arginine; the amino acid mutation at position 29 is a substitution with alanine; and the amino acid mutation at position 30 is a substitution with alanine.

(7) The virus preparation according to the above (2), which is characterized in that the syn mutation is a mutation described in the following (a), (b), (c) and/or (d):
(a) an amino acid mutation at position 796, an amino acid mutation at position 800, an amino acid mutation at position 813, an amino acid mutation at position 817, an amino acid mutation at position 854, an amino acid mutation at position 855, an amino acid mutation at position 858, an insertion of an amino acid between the amino acids at positions 816 and 817, a nonsense mutation in the amino acid at position 877, and/or a nonsense mutation in the amino acid at position 869, of SEQ ID NO: 2;
(b) an amino acid mutation at position 33, an amino acid mutation at position 40, an amino acid mutation at position 86, an amino acid mutation at position 99, an amino acid mutation at position 111, an amino acid mutation at position 121, an amino acid mutation at position 243, an amino acid mutation at position 304, and/or an amino acid mutation at position 310, of SEQ ID NO: 3;
(c) an amino acid mutation at position 49, amino acid mutations at positions 49, 50 and 51, an amino acid mutation at position 209, amino acid mutations at positions 209, 212 and 213, a nonsense mutation in the amino acid at position 217, of SEQ ID NO: 4, and/or a deletion of all of the amino acids shown in SEQ ID NO: 4; and/or (d) amino acid mutations at position 62, 63 and 64, of SEQ ID NO: 5.

(8) The virus preparation according to the above (7), which is characterized in that:
the amino acid mutation at position 796 of SEQ ID NO: 2 is a substitution with cysteine, the amino acid mutation at position 800 of SEQ ID NO: 2 is a substitution with tryptophan, the amino acid mutation at position 813 of SEQ ID NO: 2 is a substitution with isoleucine, the amino acid mutation at position 817 of SEQ ID NO: 2 is a substitution with histidine or proline, the amino acid mutation at position 854 of SEQ ID NO: 2 is a substitution with phenylalanine, the amino acid mutation at position 855 of SEQ ID NO: 2 is a substitution with valine, and the amino acid mutation at position 858 of SEQ ID NO: 2 is a substitution with cysteine or histidine;
the amino acid mutation at position 33 of SEQ ID NO: 3 is a substitution with serine, the amino acid mutation at position 40 of SEQ ID NO: 3 is a substitution with valine or threonine, the amino acid mutation at position 86 of SEQ ID NO: 3 is a substitution with proline, the amino acid mutation at position 99 of SEQ ID NO: 3 is a substitution with asparagine, the amino acid mutation at position 111 of SEQ ID NO: 3 is a substitution with valine, the amino acid mutation at position 121 of SEQ ID NO: 3 is a substitution with isoleucine, the amino acid mutation at position 243 of SEQ ID NO: 3 is a substitution with tyrosine, the amino acid mutation at position 304 of SEQ ID NO: 3 is a substitution with proline, and the amino acid mutation at position 310 of SEQ ID NO: 3 is a substitution with leucine;
the amino acid mutation at position 49 of SEQ ID NO: 4 is a substitution with alanine, the amino acid mutation at position 50 of SEQ ID NO: 4 is a substitution with alanine, the amino acid mutation at position 51 of SEQ ID NO: 4 is a substitution with alanine, the amino acid mutation at position 209 of SEQ ID NO: 4 is a substitution with alanine, the amino acid mutation at position 212 of SEQ ID NO: 4 is a substitution with alanine, and the amino acid mutation at position 213 of SEQ ID NO: 4 is a substitution with alanine; and
the amino acid mutation at position 62 of SEQ ID NO: 5 is a substitution with glycine, the amino acid mutation at position 63 of SEQ ID NO: 5 is a substitution with valine, and the amino acid mutation at position 64 of SEQ ID NO: 5 is a substitution with serine.

(9) The virus preparation according to any one of the above (1) to (8), which is characterized in that a reporter gene and/or a therapeutic gene are incorporated into the genome of the HSV.

Advantageous Effects of Invention

According to the present invention, a virus preparation comprising an oncolytic HSV having an extremely high antitumor effect is provided.

According to the present invention, a method for treating cancer, which exhibits a high therapeutic effect, is provided.

BRIEF DESCRIPTION OF DRAWINGS

FIG. 1 shows antitumor effect (1) obtained after intratumoral administration of KGNE (EGFR-retargeted RR-oHSV) and KGNE-BhKt (EGFR-retargeted RR-oHSV-syn) into U87 xenograft models. U87 cells were subcutaneously administered into a mouse, and thereafter, at a time point at which the average tumor volume reached approximately 300 mm$^3$ (9 days after the transplantation), $10^2$ and $10^3$ pfu of KGNE and $10^1$, $10^2$ and $10^3$ pfu of KGNE-BhKt were intratumorally administered. A change in the volume of the tumor over time after completion of the intratumoral administration is shown (n=6). The arrow indicates an administration day. The mean values of individual administration groups are shown. The error bar indicates a standard error.

FIG. 2 shows antitumor effect (2) obtained after intratumoral administration of KGNE and KGNE-BhKt into U87 xenograft models. U87 cells were subcutaneously administered into a mouse, and thereafter, at a time point at which the average tumor volume reached approximately 300 mm$^3$ (9 days after the transplantation), $10^2$ and $10^3$ pfu of KGNE and $10^1$, $10^2$ and $10^3$ pfu of KGNE-BhKt were intratumorally administered. A change in the volume of the tumor over time after completion of the intratumoral administration is shown (n=6). The arrow indicates an administration day. Changes in the tumor volumes of individual models over time are shown.

FIG. 3 shows antitumor effects obtained after intratumoral administration of KGNE and KGNE-BhKt into larger U87 xenograft models. U87 cells were subcutaneously administered into a mouse, and thereafter, at a time point at which the average tumor volume reached approximately 780 mm$^3$ (23 days after the transplantation), $10^7$ pfu of KGNE and $10^2$ pfu of KGNE-BhKt were intratumorally administered. A change in the volume of the tumor over time after completion of the intratumoral administration is shown (n=6). The arrow indicates an administration day. Mice, the tumor volume of which exceeded 10% of the body weight thereof, were euthanized.

FIG. 4 shows antitumor effects obtained after intravenous administration of KGNE-BhKt into U87 xenograft models. U87 cells were subcutaneously administered into a mouse, and thereafter, at a time point at which the average tumor volume reached approximately 300 mm$^3$ (8 days after the transplantation), $10^3$ to $10^7$ pfu of KGNE-BhKt were intravenously administered. A change in the volume of the tumor over time after completion of the intravenous administration is shown (n=5-6). The arrow indicates an administration day. Mice, regarding which EGFP signals could not have been confirmed from outside the bodies at the time point at which the tumor volume exceeded 10% of the body weight thereof, were euthanized.

FIG. 5 shows antitumor effects obtained after intravenous administration of KGNE-BhKt into U87 xenograft models. U87 cells were subcutaneously administered into a mouse, and thereafter, at a time point at which the average tumor volume reached approximately 730 mm$^3$ (23 days after the transplantation), $10^3$ to $10^7$ pfu of KGNE-BhKt were intravenously administered. A change in the volume of the tumor over time after completion of the intravenous administration is shown (n=5). The arrow indicates an administration day. Mice, regarding which EGFP signals could not have been confirmed from outside the bodies at the time point at which the tumor volume exceeded 10% of the body weight thereof, were euthanized.

FIG. 6 shows antitumor effects obtained after intravenous administration of KGNE-BhKt into much larger U87 xenograft models. U87 cells were subcutaneously administered into a mouse, and thereafter, at a time point at which the tumor volume reached approximately 500 to 1,800 mm$^3$ (43 days after the transplantation), $10^7$ pfu of KGNE-BhKt was intravenously administered. A change in the volume of the tumor over time after completion of the intravenous administration is shown (n=5). The arrow indicates an administration day.

FIG. 7 shows a comparison made between KGNE and KGNE-BhKt, in terms of antitumor effects obtained by systemic administration (xenograft models of human hepatoblastoma HepG2 cells). At a time point at which the tumor volume reached approximately 570 mm$^3$ (25 days after the transplantation), PBS, $10^7$ pfu of KGNE, and $10^5$ pfu and $10^7$ pfu of KGNE-BhKt were administered into the models. A change in the mean value of the tumor volume over time after the administration is shown (n=6). The arrow indicates an intravenous administration day. The error bar indicates a standard error.

FIG. 8 shows the antitumor effect of KGNEp-BhKt (EpCAM-retargeted RR-oHSV-syn) (HepG2 xenograft models). At a time point at which the tumor volume reached approximately 580 mm$^3$ (26 days after the transplantation), PBS, $10^5$ pfu of KGNE-BhKt, and $10^5$ pfu of KGNEp-BhKt were administered into the models. A change in the mean value of the tumor volume over time after the administration is shown (n=5). The arrow indicates an intravenous administration day. The error bar indicates a standard error.

FIG. 9 shows confirmation of the target specificity of RR-oHSV-syn in vivo (U87 xenograft models). At a time point at which the tumor volume reached approximately 270 mm$^3$, PBS, $10^6$ pfu of KGNE-BhKt, and $10^6$ pfu of KGNEp-BhKt were administered into the models. A change in the mean value of the tumor volume over time after the administration is shown (n=6). The arrow indicates an intravenous administration day. The error bar indicates a standard error.

FIG. 10 shows the genomic structure of an HSV used to make a comparison between RR-oHSV and CR-oHSV in terms of antitumor effects. UL: unique long segment; US: unique short segment, pCMV: human cytomegalovirus immediate early promoter (the immediate-early promoter of human cytomegalovirus); EGFP; enhanced green fluorescent protein; ΔICP34.5: deletion of ICP34.5 gene; scEGFR: EGFR-retargeted gD; Bh: R858H mutation; Kt: A40T mutation; blank box: D285N/A549T double mutation; filled box: terminal and internal inverted repeats.

FIG. 11 FIG. 11 shows the infection efficiency and cell-killing ability of gB:R858H (Bh) mutation and gK:A40T (Kt) mutation (BhKt mutation)-introduced type oHSV to U87 cells in vitro. FIG. 11A shows the shape and area of a plaque in U87 cells. Monolayer-cultured U87 cells were infected with KGΔ, KGNE, KGΔ-BhKt and KGNE-BhKt, and the cells were then cultured in a medium with methyl cellulose for 3 days, followed by observation of EGFP signals under a fluorescence microscope. The bar in the plaque image indicates 500 μm. FIG. 11B shows quantification of the EGFP-positive area (n=15). The bar in the graph indicates a mean value±standard deviation. FIG. 11C shows cell-killing ability on the U87 cells, U87 cells that had been seeded on the previous day were infected with KG, KGΔ, KGΔ-BhKt, KGNE, KGNE-BhKt and KGNEp-BhKt, and three days after the infection, an MTT assay was carried out to measure absorbance ($OD_{540}$ and $OD_{630}$) (n=6). The bar in the graph indicates a mean value±standard deviation.

FIG. 12 shows the antitumor effects of ICP34.5-deleted CR-oHSV and RR-oHSV before introduction of BhKt mutation (U87 xenograft models). At a time point at which the average tumor volume reached approximately 300 mm$^3$ (9 days after the transplantation), PBS, $10^4$ pfu and $10^7$ pfu of KGΔ, and $10^4$ pfu and $10^7$ pfu of KGNE were each administered into the xenograft models. A change in the mean value of the tumor volume over time in each administration group is shown (n=6). The arrow indicates an intratumoral administration day. The error bar indicates a standard error.

FIG. 13 shows the antitumor effects of ICP34.5-deleted CR-oHSV and RR-oHSV after introduction of BhKt mutation (U87 xenograft models). At a time point at which the average tumor volume reached approximately 320 mm$^3$ (9 days after the transplantation), PBS, $10^7$ pfu of KGΔ, $10^1$ pfu, $10^3$ pfu, $10^5$ pfu and $10^7$ pfu of KGΔ-BhKt, and $10^1$ pfu of KGNE-BhKt were each administered into the xenograft models. A change in the mean value of the tumor volume over time in each administration group is shown (n=6). The arrow indicates an intratumoral administration day. The error bar indicates a standard error.

FIG. 14 shows a comparison made between ICP34.5-deleted CR-oHSV and RR-oHSV after introduction of BhKt mutation, in terms of antitumor effects obtained by systemic administration (U87 xenograft models). (Upper view) At a time point at which the tumor volume reached approximately 700 mm$^3$ (24 days after the transplantation), PBS, $10^7$ pfu of KGΔ-BhKt, and $10^5$ pfu, $10^6$ pfu and $10^7$ pfu of KGNE-BhKt were administered. A change in the tumor volume over time after the administration is shown (n=5). The arrow indicates an intravenous administration day. Mice, the tumor volume of which exceeded 10% of the body weight thereof, were euthanized. (Lower view) The survival period of mice in the experiment shown in the upper view.

FIG. 15 shows the infection efficiency and cell-killing ability of BhKt mutation-introduced oHSV to HepG2 cells in vitro. (Upper view) Monolayer-cultured HepG2 cells were infected with KG, KGΔ, KGNE, KGΔ-BhKt, KGNE-BhKt and KGNEp-BhKt, and the cells were then cultured in a medium with methyl cellulose for 3 days, followed by observation of EGFP signals under a fluorescence microscope. The bar in the plaque image indicates 500 μm. (Center view) Quantification of the EGFP-positive area (n=15). The bar in the graph indicates a mean value±standard deviation. (Lower view) Cell-killing ability on the HepG2 cells. HepG2 cells that had been seeded on the previous day were infected with KG, KGΔ, KGΔ-BhKt, KGNE, KGNE-BhKt and KGNEp-BhKt, and three days after the infection, an MTT assay was carried out to measure absorbance ($OD_{540}$ and $OD_{630}$) (n=6). The bar in the graph indicates a mean value±standard deviation.

FIG. 16 shows a comparison made between ICP34.5-deleted CR-oHSV and RR-oHSV after introduction of BhKt mutation, in terms of antitumor effects obtained by systemic administration (HepG2 xenograft models). At a time point at which the tumor volume reached approximately 530 $mm^3$ (25 days after the transplantation), PBS, $10^7$ pfu of KGΔ-BhKt, and $10^5$ pfu and $10^7$ pfu of KGNE-BhKt were administered. A change in the mean value of the tumor volume over time after the administration is shown (n=6). The arrow indicates an intravenous administration day. The error bar indicates a standard error.

DESCRIPTION OF EMBODIMENTS

A first embodiment of the present invention relates to a virus preparation for the treatment of a cancer (hereinafter also referred to as "the virus preparation of the present invention"), comprising an HSV having a receptor-retargeted gD mutation and at least one membrane fusion activity-promoting region on the genome (hereinafter also referred to as "the HSV of the present invention").

The HSV of the present invention includes herpes simplex virus type 1 (HSV-1) and herpes simplex virus type 2 (HSV-2). The HSV-1 and HSV-2 used in the embodiment of the present invention include all strains classified into these HSVs (for example, KOS strain, F strain, 17 strain, VR3 strain, HF strain, HF10 strain, SC16 strain and the like classified into HSV-1; and 186 strain, G strain, 333 strain and the like classified into HSV-2), and all of those derived from the substrains thereof.

That is to say, for example, if HSV-1 is explained as an example, the HSV of the present invention includes, other than the KOS strain whose full-length genomic sequence is disclosed in GenBank No. JQ673480.1 (www_ncbi_nlm_nih_gov/nuccore/JQ673480.1), all of HSVs belonging to other strains classified into HSV-1 and the substrains thereof, which have a receptor-retargeted gD mutation and at least one membrane fusion activity-promoting region (for example, a region having at least one syn mutation or a membrane fusion-promoting foreign gene region).

In addition, the "membrane fusion activity-promoting region" means a region comprising a mutation or a gene for exhibiting the function of promoting the membrane fusion activity of an HSV. The mutation may be, for example, a syn mutation, and the gene may be, for example, the aftermentioned membrane fusion-promoting foreign gene.

As mentioned above, the HSV virus of the present invention having both a receptor-retargeted gD mutation and a syn mutation exhibits a significantly high antitumor effect in vivo, compared with the oncolytic HSV viruses previously reported by other groups. The significant antitumor effect of the HSV virus of the present invention that is exhibited in vivo is caused by introduction of a syn mutation, as well as a receptor-retargeted gD mutation, into the genome thereof, and this is an effect that cannot be predicted from only the data in vitro. Because of the excellent antitumor effect of the present invention, the virus preparation of the present invention can exhibit sufficient therapeutic effects, not only by intratumoral administration thereof, but also by intravenous administration thereof.

In the present description, when an amino acid mutation is described, it means a substitution of the amino acid, a deletion of the amino acid, an insertion of one or several amino acids (for example, about 1 to 10, preferably about 1 to 5, and more preferably about 1 to 3 amino acids) between the concerned amino acid and an amino acid adjacent thereto, etc., unless otherwise particularly specified. For example, when a "mutation of R21" is described while referring to a certain sequence, it means a deletion of the 21st amino acid, a substitution of the 21st amino acid with another amino acid, or an insertion of one or several amino acids between the 21st amino acid and an amino acid adjacent thereto, in the certain amino acid sequence. Besides, regarding the above-described example, it is likely that the amino acid number described in the present description is about 1 to 10 deviated from the original number, depending on each HSV strain. Accordingly, for example, when the amino acid number is ±n deviated from the original number in any given HSV strain (provided that n represents an integer of 1 or more and 10 or less), R21 is read to be R(21±n).

In the embodiment of the present invention, the "receptor-retargeted gD mutation" means a nucleotide or amino acid mutation in a gD gene or a gD protein, which comprising: a mutation to delete (or reduce) the binding ability of gD, an envelope glycoprotein playing a role in entry of an HSV virus into a cell, to bind to HVEM; a mutation to delete (or reduce) the binding ability of gD to nectin-1; a mutation to delete (or reduce) the binding ability of gD to 3-OS-HS; and a mutation to provide gD with a binding ability to a tumor antigen (for example, a mutation to insert a DNA encoding scFv or the like binding to a tumor antigen, into gD). The amino acid sequence of the gD protein of a KOS strain is shown in SEQ ID NO: 1 (not including a signal peptide consisting of 25 amino acid residues from the N-terminus).

Hereafter, specific examples of the "receptor-retargeted gD mutation" will be described below, taking the KOS strain as an example. The same applies to other strains. The gD protein of the KOS strain is encoded in the forward direction (rightward) at the position of nucleotide No. 138279 to 139463 of the KOS strain genomic sequence that has been registered under GenBank No. JQ673480.1.

The gD mutations to delete the binding ability of gD to HVEM, nectin-1, and 3-OS-HS are disclosed in many known publications such as, for example, Yoon et al., J Virol. 77: 9221-9231, 2003, Spear et al., Virology 344: 17-24, 2006, Connolly et al., J Virol. 79: 1282-1295, 2005, Uchida et al., J Virol. 83: 2951-2961, 2009, Uchida et al., J Virol. 84: 12200-12209, 2010, and Shibata et al., Gene Ther. 23: 479-488, 2016. Thus, a person skilled in the art could select a suitable mutation, as appropriate.

There is no particular limitation, but if some examples are given, examples of the position of an amino acid mutation to delete the binding ability of gD to nectin-1, which is the amino acid position of a gD protein represented by an amino acid number of SEQ ID NO: 1, may include Δ6-38 (a deletion of the amino acids at amino acid positions 6 to 38) (Menotti et al., J Virol. 82: 10153-10161, 2008), Δ61-218 (a deletion of the amino acids at amino acid positions 61 to 218) (Menotti et al., Proc Natl Acad Sci USA. 106: 9039-9044, 2009), mutations of R222 and F223, such as R222N/F223I (Uchida et al., J Virol. 83: 2951-2961, 2009), and mutations of A3 and Y38, such as A3C/Y38C (Connolly et al., J Virol. 79: 1282-1295, 2005, Uchida et al., J Virol. 83: 2951-2961, 2009).

Examples of the position of an amino acid mutation to delete the binding ability of gD to HVEM, which is the amino acid position of a gD protein represented by an amino acid number of SEQ ID NO: 1, may include: a deletion of all or a part of amino acids existing at amino acid positions 2 to 38, such as Δ7-32 (a deletion of the amino acids at amino acid positions 7 to 32) (Yoon et al., J Virol. 77: 9221-9231, 2003), Δ2-24 (a deletion of the amino acids at amino acid positions 2 to 24) (Shibata et al., Gene Ther. 23: 479-488, 2016), Δ7-11 (a deletion of the amino acids at amino acid positions 7 to 11) (Uchida et al., J Virol. 84: 12200-12209, 2010), and Δ6-38 (Menotti et al., J Virol. 82: 10153-10161, 2008); Δ61-218 (a deletion of the amino acids at amino acid positions 61 to 218) (Menotti et al., Proc Natl Acad Sci USA. 106: 9039-9044, 2009); and mutations of Q27, T29, and D30, such as Q27A, Q27P, Q27R, T29A and D30A (Spear et al., Virology 344: 17-24, 2006).

Besides, it is demonstrated that many mutations to inhibit the binding of gD to HVEM also inhibit entry of the HSV virus into cells that is mediated by 3-OS-HS (Yoon and Spear, Proc Natl Acad Sci USA. 101: 17252-17257, 2004).

In the present description, the "tumor antigen" means an antigen that is expressed specifically or at a high level on the surface of tumor (cancer) cells, such as tumor-specific antigens (TSA) or tumor-associated antigens (TAA). To date, many antigens have been reported, and a person skilled in the art could readily select such an antigen. There is no particular limitation, but if some examples are given, examples of such an antigen may include EGFR, CEA, EpCAM, CD133 (prominin-1), HER2 (epidermal growth factor receptor 2), and PSMA (prostate specific membrane antigen).

In the present description, the "mutation to provide gD with a binding ability to a tumor antigen" means a mutation, in which a DNA encoding a molecule specifically binding to a tumor antigen, such as, for example, an antibody, a peptide (including a peptide aptamer), or a protein is inserted into a gD gene, so that a gD protein fused with the molecule specifically binding to a tumor antigen can be expressed therein. The position on the gD gene, into which the DNA encoding a molecule specifically binding to a tumor antigen is to be inserted, is not particularly limited, and for example, the DNA may be inserted into the position on the gene that encodes the amino acid numbers 2 to 38 (SEQ ID NO: 1) or 61 to 218 (SEQ ID NO: 1) associated with the binding ability to HVEM.

Herein, the "antibody" may be a full-length antibody. However, the antibody may also be an antibody fragment, as long as it retains a specific binding ability to a tumor antigen. Examples of the antibody fragment may include, but are not particularly limited to, scFv (single chain Fv), Fab, Fab', F(ab')2, Fv (a variable fragment of an antibody), single-chain antibodies (a heavy chain, a light chain, a heavy chain variable region, a light chain variable region, a nanoantibody, etc.), diabody (an scFv dimer), dsFv (disulfide-stabilized Fv), and a peptide comprising CDR as at least a part thereof. Among these, a single-chain antibody, scFv, and the like are preferable.

In the embodiment of the present invention, the "syn mutation (syncytial mutation)" means a mutation introduced mainly into the gB gene (or gB protein), gK gene (or gK protein), UL20 gene (or UL20 protein: envelope protein UL20) and/or UL24 gene (or UL24 protein: nuclear protein UL24) of HSV. According to this mutation, the membrane fusion activity of the HSV is promoted. The amino acid sequence of the gB protein of the KOS strain, the amino acid sequence of the gK protein of the KOS strain, the amino acid sequence of the UL20 protein of the KOS strain, and the amino acid sequence of the UL24 protein of the KOS strain are shown in SEQ ID NO: 2, SEQ ID NO: 3, SEQ ID NO: 4, and SEQ ID NO: 5, respectively.

Hereafter, specific examples of the "syn mutation" will be described, taking the KOS strain as an example. The same applies to other strains. The gB protein of the KOS strain is encoded in the backward direction (leftward) at the position of nucleotide No. 53022 to 55736 of the KOS strain genomic sequence that has been registered under GenBank No. JQ673480.1. The gK protein of the KOS strain is encoded in the forward direction (rightward) at the position of nucleotide No. 112101 to 113117 of the same above genomic sequence. The UL20 protein of the KOS strain is encoded in the backward direction (leftward) at the position of nucleotide No. 40763 to 41431 of the same above genomic sequence. The UL24 protein of the KOS strain is encoded in the forward direction (rightward) at the position of nucleotide No. 47678 to 48487 of the same above genomic sequence. The syn mutations are also disclosed in many known publications, and thus, a person skilled in the art could select a suitable mutation, as appropriate.

Main syn mutations of the gB protein will be shown as amino acid positions of the gB protein, by using the amino acid numbers of SEQ ID NO: 2. Examples of the syn mutation of the gB protein may include R796 mutations such as R796C, R800 mutations such as R800W, T813 mutations such as T813I, L817 mutations such as L817I-1 and L817P, S854 mutations such as S854F, Δ855 mutations such as Δ855V, R858 mutations such as R858C and R858H, insertion of amino acids between E816 and L817 (VN (2-amino-acid insertion) and VNVN (4-amino-acid insertion)), a nonsense mutation of T877, and a nonsense mutation of S869.

Main syn mutations of the gK protein will be shown as amino acid positions of the gK protein, by using the amino acid numbers of SEQ ID NO: 3. Examples of the syn mutation of the gK protein may include P33 mutations such as P33S, Δ40 mutations such as A40V and A40T, L86 mutations such as L86P, D99 mutations such as D99N, A111 mutations such as A111V, T121 mutations such as T121I, C243 mutations such as C243Y, L304 mutations such as L304P, and R310 mutations such as R310L.

Main syn mutations of the UL20 protein will be shown as amino acid positions of the UL20 protein, by using the amino acid numbers of SEQ ID NO: 4. Examples of the syn mutation of the UL20 protein may include a Y49A single mutation, Y49, S50 and R51 mutations such as Y49A/S50A/R51A, an R209A single mutation, R209, T212 and R213 mutations such as R209A/T212A/R213A, a deletion of the C-terminus after N217, and a deletion of the full-length UL20 protein.

Main syn mutations of the UL24 protein will be shown as amino acid positions of the UL24 protein, by using the amino acid numbers of SEQ ID NO: 5. Examples of the syn mutation of the UL24 protein may include T62, R63 and V64 mutations such as T62G/R63V/V64S.

Main syn mutations are summarized in Table 1 below.

TABLE 1

| Gene | syn Mutation | Report regarding mutation identification |
|---|---|---|
| gK (syn 1) | P33S | Dolter et al., *J Virol* 68: 8277-81 1994 |
| | A40V | Debroy et al., *Virology* 145: 36-48 1985 |
| | | Dolter et al., *J Virol* 68: 8277-81 1994 |
| | | Israyelyan et al., *Hum Gene Ther* 18: 457-73 2007 |
| | A40T | Debroy et al., *Virology* 145: 36-48 1985 |
| | L86P | Dolter et al., *J Virol.* 68: 8277-81 1994 |
| | D99N | Dolter et al., *J Virol.* 68: 8277-81 1994 |
| | A111V | Dolter et al., *J Virol.* 68: 8277-81 1994 |
| | T121I | Dolter et al., *J Virol.* 68: 8277-81 1994 |
| | C243Y | Terry-Allison et al., *J Virol.* 72: 5802-10 1998 |
| | L304P | Dolter et al., *J Virol.* 68: 8277-81 1994 |
| | R310L | Dolter et al., *J Virol.* 68: 8277-81 1994 |
| gB (syn 3) | R796C | Gage et al., *J Virol.* 67: 2191-2201 1993 |
| | R800W | Gage et al., *J Virol* 67: 2191-2201 1993 |
| | T813I | Gage et al., *J Virol* 67: 2191-2201 1993 |
| | Insertion of 2(VN) or 4(VNVN) amino acid between E816 and L817 | Cai et al., *J Virol* 62: 2596-2604 1988 |
| | L817H | Engel et al., *Virology* 192: 112-120 1993 |
| | L817P | Diakidi-Kosta et al., *Virus Res.* 93: 99-108 2003 |
| | S854F | Walev et al., *Virus Genes* 8: 83-86 1994 |
| | A855V | Engel et al., *Virology* 192: 112-120 1993 |
| | R858C | Gage et al., *J Virol.* 67: 2191-2201 1993 |
| | R858H | Bzik et al., *Virology* 137: 185-190 1984 |
| | T877STOP (C-terminal deletion) | Baghian et al., *J Virol* 67: 2396-2401 1993 |
| | S869STOP (C-terminal deletion) | Foster et al., *Virology* 287: 18-29 2001 |
| UL20 | Y49A/S50A/R51A | Melancon et al., *J Virol.* 78: 7329-43 2004 |
| | Y49A | Melancon et al., *J Virol.* 78: 7329-43 2004 |
| | N217STOP (C-terminal deletion) | Melancon et al., *J Virol.* 78: 7329-43 2004 |
| | R209A/T212A/R213A | Melancon et al., *J Virol.* 78: 7329-43 2004 |
| | R209A | Melancon et al., *J Virol.* 78: 7329-43 2004 |
| | Deletion of UL20 itself | Baines et al., *J Virol.* 65: 6414-24 1991 |
| UL24 | T62G/R63V/V64S | Jacobson et al., *Virology* 242: 161-69 1998 |

The HSV of the present invention may not only retain the aforementioned syn mutations, but may also retain a foreign gene that promotes the membrane fusion of the HSV (hereinafter also referred to as a "membrane fusion-promoting foreign gene") in a state in which it can be expressed. The position on the HSV genome, into which the foreign gene is to be incorporated, is not particularly limited, and it may be any position on the HSV genome unless it inhibits the function of the HSV virus serving as an oncolytic virus.

The above-described membrane fusion-promoting foreign gene is not particularly limited. The membrane fusion-promoting foreign gene may be, for example, a fusogenic membrane glycoprotein (FMG) derived from a gibbon ape leukemia virus (GALV). The HSV that retains the FMG gene of GALV on the genome thereof in a state in which the gene can be expressed could readily be produced by a person skilled in the art. Such an HSV can be produced with reference to, for example, Simpson et al., Cancer Res. 66: 4835-4842, 2006, Nakamori et al., Clin Cancer Res. 9: 2727-2733, 2003, etc.

Furthermore, in the HSV of the present invention, a reporter gene and any given therapeutic gene (for example, a gene enhancing the effect of killing cancer cells, a gene suppressing the angiogenesis of a tumor, a gene promoting an antitumor immune response, etc.) and the like may be incorporated into the genome thereof, in a state in which the genes can be expressed (for details, refer to Peters et al., Mol Ther Oncolytics. 2015; 2. pii: 15010. Epub 2015 Jul. 22, etc.). The position on the HSV genome into which the aforementioned genes are to be incorporated is not particularly limited, and it may be any position on the HSV genome unless it inhibits the function of the HSV virus serving as an oncolytic virus.

The reporter gene is not particularly limited, and examples of the reporter gene may include a LacZ gene (Mineta et al., Nat Med. 1: 938-943, 1995), a Luc gene (Yamamoto et al., Gene Ther. 13: 1731-1736, 2006), a GFP gene (Adusumilli et al., FASEB J. 20: 726-728, 2006) and a NIS gene (Li et al., Cancer Gene Ther. 20: 478-485, 2013).

In addition, the therapeutic gene is not particularly limited, and examples of the therapeutic gene may include: genes encoding cytotoxic molecules, such as a CD gene (Nakamura et al., Cancer Res. 61: 5447-5452, 2001) and a TRAIL gene (Tamura et al., Mol Ther. 21: 68-77, 2013); genes encoding immunostimulatory molecules, such as a GM-CSF gene (Liu et al., Gene Ther. 10: 292-303, 2003) and an IL-12 gene (Roth et al., Ther Clin Dev. 25: 16-27, 2014); and genes encoding microenvironment regulatory molecules, such as an Angiostatin gene (Zhang et al., Mol Ther. 20: 37-45, 2012), a PF4 gene (Liu et al., Mol Ther. 14: 789-797, 2006), and a Chondroitinase-ABC gene (Dmitrieva et al., Clin Cancer Res. 17: 1362-1372, 2011).

The virus preparation of the present invention comprises at least one HSV of the present invention, and may also comprise pharmaceutically acceptable components, buffers, excipients, adjuvants, antiseptics, fillers, stabilizers, thickeners, and other components generally used in formulation. Moreover, depending on the situation, the virus preparation of the present invention may further comprise therapeutically effective other oncolytic viruses and/or therapeutically effective drugs such as anticancer agents and auxiliary components (e.g., immune checkpoint inhibitors such as CTLA-4 blockers and PD-1 antibodies, immunostimulants such as GM-CSF, etc.), as well as the HSV of the present invention.

The dosage form of the virus preparation of the present invention is not particularly limited, and it may be any dosage form, as long as it is a form suitable for the administration method, the administration route, the preservation method, etc. The virus preparation of the present invention may be formulated into a dosage form that can be selected by any person skilled in the art, and examples of the dosage form may include liquids such as a solution and a suspension, and solids or semi-solids, such as an emulsion, a tablet, a pellet, and a capsule.

The types of pharmaceutical additives used in the production of the virus preparation of the present invention, the ratio of the pharmaceutical additives to the active ingredient, or the method for producing the present virus preparation can be appropriately selected by a person skilled in the art, depending on the form of the present virus preparation. The pharmaceutical additive that can be used herein is an inorganic or organic substance, or a solid or liquid substance. The pharmaceutical additive can be generally mixed into the present virus preparation, in an amount of 1% by weight to 90% by weight with respect to the weight of the active ingredient. Specific examples of such a substance may include lactose, glucose, mannitol, dextrin, cyclodextrin, starch, sucrose, magnesium aluminometasilicate, synthetic aluminum silicate, carboxymethyl cellulose sodium, hydroxypropyl starch, carboxymethyl cellulose calcium, ion exchange resin, methyl cellulose, gelatin, gum Arabic, hydroxypropyl cellulose, hydroxypropyl methyl cellulose, polyvinylpyrrolidone, polyvinyl alcohol, light anhydrous silicic acid, magnesium stearate, talc, tragacanth, bentonite, veegum, titanium oxide, sorbitan fatty acid ester, sodium lauryl sulfate, glycerin, fatty acid glycerin ester, purified lanolin, glycerogelatin, polysorbate, macrogol, vegetable oil, wax, liquid paraffin, white petrolatum, fluorocarbon, nonionic surfactant, propylene glycol, and water.

In particular, when the virus preparation of the present invention is produced in the form of a liquid such as an injection or an intravenous drip, the active ingredient is dissolved in distilled water for injection, as necessary, together with a pH adjuster such as hydrochloric acid, sodium hydroxide, lactic acid, sodium monohydrogen phosphate, or sodium dihydrogen phosphate, and a tonicity agent such as sodium chloride or glucose, and the obtained solution is then subjected to aseptic filtration, and the resulting solution is then filled into an ampoule. Otherwise, mannitol, trehalose, saccharose, sorbitol, dextrin, cyclodextrin, gelatin and the like are further added to the resulting solution, followed by vacuum lyophilization, so that an injection that is soluble when used may be produced. Alternatively, lecithin, polysorbate 80, polyoxyethylene hardened castor oil and the like are added to the above resulting solution, and the obtained mixture is then emulsified in water, so that an emulsion for injection may also be produced.

Moreover, the virus preparation can be formulated into a liquid or a solid form such as freeze-dried powder, which is in a conservable state. Such a virus preparation may be produced by applying a method known in the present technical field, for example, the method disclosed in WO98/02522, WO03/053463, WO2007/056847, WO2008/114021, WO2014/053571, etc., and appropriately modifying the method.

The virus preparation of the present invention may be administered by any administration route, as long as it is a route capable of dissolving a tumor. Examples of the administration route of the present virus preparation may include intratumoral administration and intravenous administration. In particular, since the virus preparation of the present invention has an extremely high oncolytic effect, it can exhibit a sufficient antitumor effect at a low dose and/or at a small number of doses, in comparison to known oncolytic virus preparations, even by intravenous administration.

The applied dose and the number of doses of the virus preparation of the present invention are not particularly limited, and the applied dose and the number of doses can be selected, as appropriate, by a doctor's judgment, depending on conditions such as therapeutic purpose, the type of a cancer, the body weight and age of a patient, and the severity of the disease.

Upon administration of the virus preparation of the present invention, various unit doses may be included. The unit dose means a predetermined content of the HSV of the present invention. This unit dose may be administered as a single injection, or as a continuous injection over a predetermined period of time. Furthermore, the number of doses may be either a single administration or multiple administrations.

The virus preparation of the present invention exhibits the effect of suppressing a tumor increase, when it is administered at a unit dose smaller than the effective dose of the previously reported oncolytic HSV viruses (i.e., a dose at which the effect of suppressing a tumor increase is exhibited), and for example, in the case of intratumoral administration, at a dose of approximately $10^{-6}$ to approximately $10^{-5}$ of the dose (pfu) of the preceding oncolytic viruses (see FIG. 4 of Non Patent Literature 10, FIG. 6 of Non Patent Literature 11, etc.).

Since the HSV of the present invention has a receptor-retargeted gD mutation, it is capable of lysing (killing) cells (tumor cells), as long as a tumor antigen is expressed on the surface of the cells. Accordingly, the cancer that is a therapeutic target of the virus preparation of the present invention is not particularly limited, and it may be any cancer. If representative cancers are exemplified, examples of the cancer may include: malignant tumors such as hepatocellular carcinoma, intrahepatic bile duct carcinoma, renal cell carcinoma, squamous cell carcinoma, basal cell carcinoma, transitional cell carcinoma, adenocarcinoma, malignant gastrinoma, melanoma, fibrosarcoma, mucinous sarcoma, liposarcoma, leiomyosarcoma, rhabdomyosarcoma, malignant teratoma, hemangiosarcoma, Kaposi's sarcoma, osteosarcoma, chondrosarcoma, lymphangiosarcoma, malignant meningioma, non-Hodgkin's lymphoma, Hodgkin's lymphoma, leukemia, and brain tumor; malignant neoplasms including epithelial cell-derived neoplasm (epithelial carcinoma), basal cell carcinoma, adenocarcinoma, lip cancer, oral cancer, esophageal cancer, gastrointestinal cancers such as small intestine cancer and stomach cancer, colon cancer, rectal cancer, liver cancer, bladder cancer, pancreatic cancer, ovarian cancer, cervical cancer, lung cancer, breast cancer, skin cancers such as squamous cell carcinoma and basal cell carcinoma, prostate cancer, and renal cell carcinoma; and other known cancers that impair epithelial, mesenchymal, or blood cells in a whole body.

A second embodiment of the present invention relates to a therapeutic method for treating a cancer (regression of a tumor), which comprises administering a virus preparation comprising an HSV virus having a receptor-retargeted gD mutation and at least one syn mutation to a patient (including mammals other than humans) (hereinafter also referred to as "the method for treating a cancer of the present invention"). The method for treating a cancer of the present invention includes a treatment performed for the purpose of regression of a previously generated tumor, and a treatment performed for the purpose of killing metastasized cancer cells in the case of predicting metastasis. The present method for treating a cancer also includes an adjuvant therapy performed before or after a surgical operation.

The "mammal" as a target of the treatment means any given animal classified into Mammalia, and the mammal is not particularly limited. Examples of the mammal used herein may include all animals including humans, companion animals such as a dog, a cat and a rabbit, livestock animals such as a bovine, a swine, sheep and a horse. The mammal is preferably a human.

When an English translation of the present description includes singular terms with the article "a," "an," and "the," these terms include not only single items but also multiple items, unless otherwise clearly specified from the context.

Hereinafter, the present invention will be further described in the following examples. However, these examples are only illustrative examples of the embodiments of the present invention, and thus, are not intended to limit the scope of the present invention.

EXAMPLES

In the present Examples, antitumor effects obtained when the virus preparation of the present invention is administered to subcutaneous tumor mouse models via intratumoral administration and intravenous administration are shown. As mentioned below, it could be confirmed that the virus preparation of the present invention exhibits an extremely excellent antitumor effect, compared with known oncolytic HSV virus preparations.

1. Materials and Methods 1-1. Cells

The human glioma cell line U87 (ATCC HTB-14) was cultured using an Eagle's minimal essential medium (E-MEM; FUJIFILM Wako Pure Chemical Corporation, Osaka) supplemented with 10% FBS (THERMO FISHER SCIENTIFIC, Waltham, MA). The human hepatoblastoma cell line HepG2 (ATCC HB-8065) was cultured using Dulbecco's modified Eagle's medium (DMEM, THERMO FISHER SCIENTIFIC) supplemented with 10% FBS. The monkey kidney cell line Vero (ATCC CCL-81) was cultured using DMEM supplemented with 5% FBS. A substrain (Vero-EpCAM) obtained by introducing human EpCAM into the monkey kidney cell line Vero (ATCC CCL-81) was cultured using a Dulbecco's modified Eagle's medium (DMEM, THERMO FISHER SCIENTIFIC) supplemented with 5% FBS, to which 4 μg/mL puromycin (THERMO FISHER SCIENTIFIC) was added (see Non Patent Literature 5). The U87 cells were cultured in a flask coated with Cellmatrix type I-P (NITTA GELATIN INC., Osaka).

It was confirmed that no mycoplasma was mixed into all of the aforementioned cells.

1-2. Viruses and Purification Methods

As viruses (KGNE-BhKt and KGNEp-BhKt) prepared by introducing a syn mutation (gB: R858H and gK: A40T) into gB and gK of EGFR-retargeted RR-oHSV (KGNE) and EpCAM-retargeted RR-oHSV, the previously reported viruses were used (Non Patent Literature 5 and Non Patent Literature 9). These viruses express EGFP under the control of the immediate early promoter of cytomegalovirus, and has a cell entry-enhancing double mutation in gB (gB: D285N/A549T) (Non Patent Literature 7).

Plasmids (pKG, pKGΔ, and pKGΔ-BhKt) encoding the viral genomes of a virus (KG) prepared by introducing an expression cassette of EGFP into KOS-37 BAC (Gierasch et al., J Virol Methods. 135: 197-206, 2006), a virus (KGΔ) comprising a deletion of the ICP34.5 gene of KG, and a virus (KGΔ-BhKt) prepared by introducing a syn mutation (gB: R858H and gK: Δ40T) into the gB and gK of KGΔ, were produced by genetic modification based on a Red homologous recombination system (Tischer et al., Biotechniques 40: 191-197, 2006). In short, the expression cassette of EGFP was introduced into a BAC plasmid encoding the viral genome of KOS-37 BAC (provided by David Leib, Dartmouth Medical School) according to a method similar to the previously reported method, so as to produce pKG (Non Patent Literature 5). A primer set (5'-CCCAGGTAACCTCCACGCCCAACTCG-GAACCCGTGGTCAGGAGCGCGCCCA GGATGACGACGATAAGTAGGG-3' (SEQ ID NO: 6) and 5'-GACGACTCGGCGGACGCTGGTTGGCCGGGC-CCCGCCGCGCTGGCGGCCGC GGGCGCGCTCCTGAC-CACGGGTTCCGAGTTGGGCGTGGAGGT-TACCTGGGC TACAACCAATTAACCAATTCT-GATTAG-3' (SEQ ID NO: 7)) was used, and a sequence obtained by amplification of a kanamycin resistance gene sandwiched between the recognition sequences of I-Sce I encoded by pEPkan-S2 (provided by Nikolaus Osterrieder, Free University of Berlin) was used as a targeting fragment. The ICP34.5 gene of pKG was deleted to produce pKGΔ. Since two copies of ICP34.5 were present on the viral genome, the operation to delete the 2 copies was carried out for each one copy at 2 stages. A syn mutation (gB: R858H and gK: Δ40T) was introduced into the gB and gK of pKGΔ according to a method similar to the previously reported method, so as to produce pKGΔ-BhKt (Non Patent Literature 9). All of the constructs were subjected to a PCR analysis, a pulsed-field gel electrophoresis analysis following restriction enzyme digestion, and DNA sequence analysis, and it was thereby confirmed that modification of interest was properly carried out on the constructs. KG, KGΔ, and KGΔ-BhKt were produced by co-transfection of Vero cells with pKG, pKGΔ, and pKGΔ-BhKt, together with pxCANCre (provided by Izumu Saito, The University of Tokyo), and the produced KG, KGΔ, and KGΔ-BhKt were then subjected to limiting dilution twice with Vero cells, so that the obtained monoclones thereof were used. It was confirmed by the previously reported method that a BAC sequence was removed from the obtained monoclones (Miyagawa et al., Proc Natl Acad Sci USA. 112: E1632-1641, 2015).

Virus stocks used in animal experiments were prepared as mentioned below. Monolayer-cultured Vero-EpCAM cells were infected with KG, KGΔ and KGNE (MOI: 0.03), with KGNEp (MOI: 0.06), with KGΔ-BhKt and KGNE-BhKt (MOI: 0.003), and with KGNEp-BhKt (MOI: 0.006) at 37° C. until the following day. From the following day, the cells were cultured at 33° C. for 4 days. Five days after initiation of the infection, 5 M NaCl was added in an amount of ⅒ to the culture solution, and the obtained solution was then cultured at 33° C. until the following day. On the following day, the culture solution was shaken at room temperature for 60 minutes, so that all of the cells were exfoliated. The culture solution was recovered together with the cells, and was then centrifuged at 4° C. at 2, 100×g for 15 minutes. Thereafter, the supernatant was filtrated through a 0.8-μm nitrocellulose membrane filter (THERMO FISHER SCIENTIFIC), and the filtrate was then centrifuged at 4° C. at 48,500×g for 30 minutes. Thereafter, the supernatant was removed, followed by re-suspension in Dulbecco's phosphate buffered saline (PBS; Sigma, St. Louis, MO). An $MgCl_2$ aqueous solution was added to the solution to a final concentration of 2 mM, and BENZONASE (registered trademark) Nuclease (MERCK, Darmstadt, Germany) was then added to the obtained solution to a final concentration of 300 units/mL. Inversion mixing was gently performed on the thus obtained solution at room temperature for 1 hour. Thereafter, the reaction solution was diluted with PBS, and was then centrifuged at 4° C. at 48,500×g for 30 minutes, and the supernatant was then removed. PBS was added again, the solution was then centrifuged at 4° C. at 48,500×g for 30 minutes, and the supernatant was then removed. A small amount of PBS was gently added, and the obtained mixture was then left at rest at 4° C. until the following day. On the following day, pellets were disaggregated by pipetting and with the use of an 18G needle, a 21G needle, a 24G needle, a 27G needle, and a 30G needle (TERMO, Tokyo, Japan), and were then dispensed in small amounts to obtain small portions. The obtained small portions were quickly frozen with liquid nitrogen, and were then preserved at −80° C. The plaque-forming unit (pfu) concentration (pfu/mL) of all of the viruses was determined by obtaining a mean value of the measurement values obtained by measuring an infectious titer, three times independently, using Vero-EpCAM cells.

1-3. Plaque Formation Assay and Cell Killing Assay 1-3-1. Plaque Formation Assay On the previous day, the cells were seeded on a 6-well plate, and each virus was then added in an amount of 30 pfu/well or 100 pfu/well to the monolayer-cultured cells. The thus obtained mixture was cultured at 37° C. for 2 hours, and thereafter, a 1% methyl cellulose-containing medium was overlayered on the culture, followed by culturing the mixture at 37° C. for 3 days. The fluorescence image of EGFP was taken using a BZ-X700 microscope (KEYENCE, Osaka, Japan). The plaque area was analyzed using Hybrid Cell Count software BZ-H3C (KEYENCE).

1-3-2. Cell Killing Assay

On the previous day, the cells were seeded on a 96-well plate, and each virus was then added to the monolayer-cultured cells, to result in MOI of 0.001, 0.01 or 0.1. The thus obtained mixture was cultured at 37° C. for 3 days. Thereafter, the supernatant was removed, and 0.5 mg/mL MTT in PBS (−) was then added, followed by culturing the mixture at 37° C. for 1 hour. Thereafter, the supernatant was removed, and 99% ethanol was then added, followed by performing incubation at room temperature for 30 minutes. Thereafter, the absorbances at $OD_{540}$ and $OD_{630}$ were measured using Synergy NEO2 (BIOTEK, Winooski, USA).

1-4. Animal Experiments

All animal experiments were approved by the Animal Experiment Expert Committee, the University of Tokyo, and were performed by methods that complied with Rules of Animal Experiments, the University of Tokyo, and Animal Experiment Implementation Manuals, the University of Tokyo. Into the left abdominal subcutis of 6 to 8-week-old female severe combined immunodeficient mice SCID-Beige (CB17.Cg-Prkdc$^{scid}$Lyst$^{bg-J}$/CrlCrlj; CHARLES RIVER LABORATORIES JAPAN, INC., Kanagawa), various types of human cancer cell lines each suspended in a Hanks' balanced salt solution (THERMO FISHER SCIENTIFIC) were transplanted in each amount of $1\times10^7$ cells/100 µL. The mice were grouped, so that the mean value of tumor volumes could be approximated to a time point at which the mean value of tumor volumes reached the value described in Description of Drawings. PBS and a virus suspended in PBS were administered in a volume of 30 µL to the mice via intratumoral administration, or PBS and a virus suspended in PBS were administered in a volume of 200 µL to the mice via intravenous administration through the right caudal vein. The intratumoral administration was carried out by administering the sample through one point of a tumor, into which a needle was inserted so that about two-thirds of its length was beneath the tumor in the long axis direction of the tumor. For the transplantation of cells and administration of viruses, a 27G needle was used, and a needle independently prepared to each mouse was used to avoid the share use of a needle. The expression of EGFP in the tumor was confirmed by using a wavelength interchangeable twin arm LED irradiation device (OPTOCODE CORPORATION, Tokyo). The tumor volume was obtained according to the formula: (major axis×minor axis2)/2 (Tomayko et al., Cancer Chemother Pharmacol. 24:148-154, 1989).

1-5. Statistical Analysis

All statistical analyses were carried out using Prism 8 for macOS version 8.2.0 (272). The statistical analysis of the plaque formation assay was carried out according to a Dunn's multiple comparison test. On the other hand, the statistical analysis of the cell killing assay was carried out according to a Turky's multiple comparison test. Further, the statistical analysis of a tumor volume was carried out according to a 2-way repeated measure ANOVA, and the statistical analysis of a survival rate was carried out according to a log-lank test. In all of these statistical analyses, when the P value was less than 0.05, it was judged that there was a significant difference.

2. Results 2-1. Studies Regarding In Vivo Effects of RR-oHSV 2-1-2. Comparison Regarding Antitumor Effects on Human Glioma Subcutaneous Tumor Models by Intratumoral Administration In order to examine whether two syn mutations (BhKt mutations) with enhanced cell-to-cell spread efficiency and cell-killing ability, which converted a cell-to-cell spread mode of RR-oHSV to a cell-to-cell spread mode attended with formation of multinucleated giant cells in vitro, enhance the antitumor effect of RR-oHSV in vivo, the antitumor effects of KGNE and KGNE-BhKt on human glioma cell line U87 xenograft models (Non Patent Literature 10 and Non Patent Literature 11), which had been frequently used to examine the antitumor effect of oHSV, were evaluated. It has been confirmed that the U87 cell line is EGFR-positive, and that a significant antitumor effect is found in the U87 cells by intratumoral administration of $10^7$ pfu of KGNE (Non Patent Literature 6).

The infectivity of KGNE and KGNE-BhKt in the U87 cells was examined in vitro. As a result, it was confirmed that the U87 cells started to form multinucleated giant cells as a result of the introduction of BhKt mutations, and that cell-to-cell spread efficiency and cell-killing ability were significantly enhanced. In order to examine the influence of the introduction of such a BhKt mutation on antitumor effects in vivo, when the tumor volume of mouse models with subcutaneous transplantation of U87 cells reached approximately 300 mm$^3$, KGNE and KGNE-BhKt were directly administered into a site around the center of the tumor. As a result, it was found that a $10^2$ pfu KGNE administration group did not exhibit a significant antitumor effect, compared with a PBS administration group (p=0.62), whereas a $10^3$ pfu KGNE administration group exhibited a significant antitumor effect (p<0.0001) (FIG. 1). Among the mice of the $10^3$ pfu KGNE administration group, tumor regression was observed in one mouse. In contrast, in the KGNE-BhKt administration groups, tumor regression was observed at all types of doses, and all of the KGNE-BhKt administration groups exhibited a significantly high antitumor effect, compared with the $10^3$ pfu KGNE administration group (p<0.0001) (FIG. 1). In the KGNE-BhKt administration groups, tumor regression was observed in all mice (FIG. 2). From these results, it was suggested that the in vivo antitumor effect of RR-oHSV was at least 100 times or more enhanced by introduction of a BhKt mutation.

Although the following is the results of an in vitro experiment, it has been reported that KGNE-Bh as a syn mutation introduced only into gB and KGNE-Kt as a syn mutation introduced only into gK have more excellent cell-to-cell spread efficiency than KGNE (without syn mutation) (Non Patent Literature 9). Accordingly, it is considered that even an HSV having a syn mutation introduced only into either gB or gK could exhibit in vivo an antitumor effect more excellent than that of KGNE (without syn mutation).

2-1-2. Comparison Regarding Antitumor Effects on More Enormous Tumor Models by Intratumoral Administration In order to examine whether or not intratumoral administration of KGNE-BhKt also exhibits an antitumor effect on a tumor more enormous than those in the reports of various researchers, when the tumor volume reached approximately 780 mm$^3$, $10^7$ pfu of KGNE and $10^2$ pfu of KGNE-BhKt were intratumorally administered, and the antitumor effect was then examined. In a PBS administration group, the tumor of all mice reached 10% of the body weight in the measurement performed 10 days after the intratumoral administration. On the other hand, in a KGNE administration group, the tumor of 5 out of 6 mice reached 10% of the body weight at 10 days after the intratumoral administration, and in a KGNE-BhKt administration group, the tumor of only 1 out of 6 mice reached 10% of the body weight at 10 days after the intratumoral administration (FIG. 3). Although KGNE-BhKt was administered at a dose of 1/100,000 of the dose of KGNE, rapid tumor regression was observed in 5 out of 6 mice, and the tumors of these mice resulted in complete regression (FIG. 3). No signs of the regrowth of the tumor were observed during the observation period. From these results, it was suggested that KGNE-BhKt has an antitumor effect that is 100,000 times or more stronger than that of KGNE. In addition, no abnormalities were found in the mice of the KGNE-BhKt administration group, and after the finding of the tumor regression, no significant body weight reduction was found in all of the mice until the final measurement day. Accordingly, it was suggested that, even after introduction of a syn mutation such as a BhKt mutation into an HSV, the HSV maintains high safety.

2-1-3. Studies Regarding Antitumor Effects Obtained by Systemic Administration

High antitumor effects and high safety were obtained by intratumoral administration of KGNE-BhKt. Thus, KGNE-BhKt was administered to the same mouse models as those described above by intravenous administration, and the obtained antitumor effect was then examined. When the tumor volume reached approximately 300 mm$^3$, $10^3$ to $10^7$ pfu of KGNE-BhKt were administered through the caudal vein of the mice. As a result, tumor regression was observed in 1 out of 5 mice by $10^3$ and $10^4$ pfu of intravenous administration, in 2 out of 5 mice by $10^5$ pfu of intravenous administration, and in all of the mice by $10^6$ and $10^7$ pfu of intravenous administration (FIG. 4). From these results, it was suggested that KGNE-BhKt is capable of regression of a tumor, even when it is administered at a dose of $10^3$ pfu by intravenous administration, and that KGNE-BhKt is capable of complete regression of the tumor of all of the mice by increasing the dose thereof.

In order to examine the influence of a difference in tumor volumes upon intravenous administration of KGNE-BhKt on the antitumor effects obtained after the administration thereof, when the tumor volume reached approximately 730 mm$^3$, the same experiment as described above was carried out. As a result, tumor regression was not observed in any mice by intravenous administration at a dose of $10^3$ pfu, but complete tumor regression was observed in 1 out of 5 mice by intravenous administration at a dose of $10^4$ pfu, and in all of the mice by intravenous administration at doses of $10^5$, $10^6$ and $10^7$ pfu (FIG. 5). From these results, it was suggested that when KGNE-BhKt is administered to a larger tumor volume, tumor regression effects can be obtained at a smaller dose.

Considering the above-described research results, KGNE-BhKt was administered to mice via intravenous administration, when the volume of a subcutaneous tumor reached approximately 500 to 1,800 mm$^3$. As a result, rapid tumor regression was observed in all of the mice (FIG. 6). From these results, it was suggested that intravenous administration of KGNE-BhKt is capable of regression of a tumor even having a tumor volume of approximately 1,800 mm$^3$. In all of the studies regarding intravenous administration of KGNE-BhKt, no abnormalities were found in all of the mice, and after the finding of the tumor regression, no significant body weight reduction was found in all of the mice until the final measurement day. Accordingly, it was suggested that KGNE-BhKt can be safely administered via systemic administration.

2-1-4. Comparison Between KGNE and KGNE-BhKt in Terms of Antitumor Effects Obtained by Systemic Administration In order to make a comparison between KGNE and KGNE-BhKt in terms of antitumor effects, when the tumor volume of HepG2 subcutaneous tumor models reached approximately 570 mm$^3$, KGNE and KGNE-BhKt were each administered to the models once by intravenous administration (FIG. 7). The antitumor effects of individual viruses obtained until 11 days after the administration of the viruses, at which the mice of a PBS administration group reached an endpoint (a time point at which the tumor volume exceeded 10% of the body weight), were compared with the antitumor effects found in the PBS administration group. As a result, significantly high antitumor effects were found in a $10^7$ pfu KGNE administration group and in KGNE-BhKt administration groups at both types of doses (p<0.0001). The antitumor effects found in the KGNE administration group until 21 days after the mice of the KGNE administration group reached the endpoint were compared with the antitumor effect found in the KGNE-BhKt administration group. As a result, a significantly higher antitumor effect was found in the KGNE-BhKt administration groups at both types of doses, than in the $10^7$ pfu KGNE administration group ($10^5$ pfu: p=0.048, $10^7$ pfu: p<0.0001). From these results, it was suggested that KGNE-BhKt exhibits at least 100 times or more higher antitumor effect on the HepG2 subcutaneous tumor models, than KGNE does. From the aforementioned results, it was suggested that the antitumor effect of RR-oHSV on various cancer cells can be enhanced by introduction of a BhKt mutation.

2-1-5. Antitumor Effects of RR-oHSV-Syn that Targets EpCAM (Epithelial Cell Adhesion Molecule, CD326)

In order to examine whether or not RR-oHSV-syn targeting a molecule different from EGFR also exhibits an antitumor effect, when the tumor volume of HepG2 subcutaneous tumor models reached approximately 580 mm$^3$, KGNEp-BhKt and KGNE-BhKt were each administered to the models once by intravenous administration (FIG. 8). The antitumor effects of individual viruses obtained until 8 days after the administration of the viruses, at which the mice of a PBS administration group reached the endpoint, were compared with the antitumor effects found in the PBS administration group. As a result, both of the virus administration groups exhibited a significantly high antitumor effect (p<0.0001). On the other hand, no significant difference was found between the KGNE-BhKt administration group and the KGNEp-BhKt administration group until the measurement at 18 days after the administration (p=0.15). However, from the measurement at 21 days after the administration, a significant difference appeared to be observed, and such a significant difference was also observed even in the results obtained until termination of the experiment (42 days after the administration) (p=0.0045). From these results, it was suggested that RR-oHSV-syn can exhibit an antitumor effect, regardless of the type of a target molecule, but that the level of such an antitumor effect may be different.

In order to examine whether or not RR-oHSV-syn maintains target specificity even in vivo and does not exhibit an antitumor effect on cancer cells that do not express target molecules, when the tumor volume of subcutaneous tumor models with EpCAM-negative U87 cells reached approximately 270 mm$^3$, KGNEp-BhKt and KGNE-BhKt were each administered to the models once by intravenous administration at a dose 10 times higher than the dose exhibiting a significant antitumor effect on HepG2 (FIG. 9). The antitumor effects of individual viruses obtained until 18 days after the administration of the virus, at which the mice of a PBS administration group reached the endpoint, were compared with the antitumor effects found in the PBS administration group. As a result, a KGNE-BhKt administration group exhibited a significantly high antitumor effect (p<0.0001), whereas a KGNEp-BhKt administration group did not have a significant difference from the PBS administration group (p=0.90). From these results, it was suggested that RR-oHSV-syn does not exhibit an antitumor effect on the tumors of cancer cells that do not express target molecules, and that the target specificity of RR-oHSV-syn is maintained even in vivo.

2-2. Comparison Between RR-oHSV and CR-oHSV in Terms of Antitumor Effects

CR-oHSV with attenuated proliferation efficiency in normal cells has been reported, so far. As CR-oHSV having a syn mutation, an HSV having a deletion of one or more of ICP34.5, ICP6, ICP0, ICP4, and UL56 has been reported (Fu et al., Cancer Res. 62: 2306-2312, 2002, Nakamori et al., Clin Cancer Res. 9: 2727-2733, 2003, Nakamori et al., Prostate 60: 53-60, 2004, Fu et al., Int J Oncol. 30: 1561-1567, 2007, Nakamori et al., Mol Ther. 9: 658-665, 2004, Israyelyan et al., Hum Gene Ther. 18: 457-473, 2007, Israyelyan et al., Virol J. 5: 68, 2008, Takaoka et al., Virol J. 8: 294, 2011).

Hence, studies were made regarding a difference generated between the antitumor effect of the RR-oHSV of the present invention having a syn mutation and the antitumor effect of CR-oHSV having a syn mutation.

2-2-1. Structure of BhKt Mutation-Introduced Type oHSV

In order to compare the antitumor effect of RR-oHSV with the antitumor effect of CR-oHSV, the ICP34.5 gene of an HSV (KG) that expresses EGFP under the control of a CMV promoter was deleted to produce CR-oHSV (KGΔ) (FIG. 10). To examine the effect obtained by introduction of a BhKt mutation, a BhKt mutation was introduced into KGΔ to produce KGΔ-BhKt (FIG. 10). As control RR-oHSVs, KGNE and KGNE-BhKt were used (FIG. 10).

2-2-2. In Vitro Infection Efficiency and Cell-Killing Ability of BhKt Mutation-Introduced Type oHSVs (RR-oHSV and CR-oHSV) on U87 Cells Whether or not the form of a plaque in U87 cells is changed to a form attended with multinucleated giant cells by introduction of a BhKt mutation was examined. As a result, the plaque forms of KGΔ and KGNE were changed to forms attended with the formation of multinucleated giant cells by introduction of a BhKt mutation (FIG. 11A). Moreover, the areas of the formed plaques were compared with one another. As a result, the BhKt mutation-introduced type RR-oHSV formed a significantly larger plaque than the parent strain did. No significant difference was found between the plaque areas of BhKt mutation-introduced viruses (FIG. 11B).

Individual viruses were compared with one another in terms of cell-killing ability on U87 cells. As a result, it was suggested that the BhKt mutation-introduced type oHSV has a higher cell-killing ability than the parent strain at all of the MOI values examined (FIG. 11C). It was also suggested that the cell-killing ability of KGΔ-BhKt was equivalent to the cell-killing ability of KGNE-BhKt (FIG. 11C).

From the aforementioned results, it was suggested that, in terms of the effect of in vitro introduction of a BhKt mutation to enhance the cell-to-cell spread ability and cell-killing ability, ICP34.5-deleted CR-oHSV was equivalent to EGFR-retargeted RR-oHSV.

2-2-3. Antitumor Effects of ICP34.5-Deleted CR-oHSV and RR-oHSV on Subcutaneous Tumor Models with U87 Cells Before Introduction of BhKt Mutation For studies regarding the presence or absence of the enhancement of the antitumor effects of oHSV by introduction of a BhKt mutation, in order to find a dose at which KGΔ as a parent strain and KGNE did not exhibit toxicity but exhibit significant antitumor effects, $10^4$ pfu or $10^7$ pfu of the virus was intratumorally administered once to xenograft models obtained by subcutaneous transplantation of U87 cells into severe immunodeficient mice (FIG. 12). Some mice, into which $10^7$ pfu of KG had been administered, were observed to have a skin lesion from the tumor to the dorsal portion 9 days after the administration, and the skin lesion was enlarged to such an extent that the tumor volume became unmeasurable 15 days after the administration. In some mice, into which $10^4$ pfu of KG had been administered, a similar skin lesion was observed 12 days after the administration, and the skin lesion was enlarged to such an extent that the tumor volume became unmeasurable 18 days after the administration. In the $10^7$ pfu KG administration group, all of 6 mice died before the mice reached the endpoint, and in the $10^4$ pfu KG administration group, 2 mice died. In contrast, in all mice into which KGΔ or KGNE had been administered, a skin lesion, which was observed in the KG-administered mice, could never be confirmed, and no mice died before the mice reached the endpoint. From these results, it was suggested that toxicity is attenuated after intratumoral administration due to a deletion of ICP34.5 or a receptor-retargeting modification. Under conditions of administration of $10^7$ pfu of the virus, the KGΔ administration group and the KGNE administration group exhibited significant antitumor effects, compared with the PBS administration group (KGΔ: p=0.0005, KGNE: p<0.0001). Under conditions of administration of $10^4$ pfu of the virus, the KGΔ administration group did not exhibit significant antitumor effects compared with the PBS administration group, whereas the KGNE administration group exhibited significant antitumor effects (KGΔ: p=0.77, KGNE: p<0.0001). In addition, when the antitumor effects of KGΔ were compared with the antitumor effects of KGNE, a significant difference was found under conditions of administration of $10^7$ pfu of the virus (p<0.0001). Moreover, such a significant difference was not found between conditions of administration of $10^4$ pfu of KGNE and $10^7$ pfu of KGΔ (p=0.43). From these results, it was suggested that KGNE can exhibit a higher antitumor effect than KGΔ, and thus that KGNE can exhibit an antitumor effect equivalent to that of KGΔ, when KGNE is used in a virus amount that is 1/1000 of KGΔ.

2-2-4. Influence of Introduction of BhKt Mutation on Antitumor Effects of ICP34.5-Deleted CR-oHSV and RR-oHSV In order to examine whether or not the antitumor effects of ICP34.5-deleted CR-oHSV are enhanced by introduction of a BhKt mutation, when the volume of a subcutaneous tumor of U87 cells reached approximately 300 mm$^3$, ICP34.5-deleted CR-oHSV was intratumorally administered once, and the antitumor effects thereof were then examined (FIG. 13). When compared with a PBS administration group, in a $10^1$ pfu KGΔ-BhKt administration group, a significant antitumor effect was not observed (p=0.72), but in a mouse group into which $10^3$ pfu or more of KGΔ-BhKt had been administered, a significantly high antitumor effect was observed ($10^3$ pfu: p=0.0041, $10^5$ pfu and $10^7$ pfu: p<0.0001). Moreover, a mouse group, into which $10^5$ pfu or more of KGΔ-BhKt was administered, exhibited a higher antitumor effect than a $10^7$ pfu KGΔ administration group ($10^5$ pfu: p=0.0066, $10^7$ pfu: p<0.0001). From these results, it was suggested that the antitumor effect of ICP34.5-deleted CR-oHSV is at least 100 times enhanced by introduction of a BhKt mutation. However, even if $10^7$ pfu of KGΔ-BhKt was administered to the KGΔ-BhKt administration group, tumor enlargement was just temporarily suppressed. On the other hand, in the KGNE-BhKt administration group, the tumors of all mice resulted in complete regression due to administration of $10^1$ pfu of the virus, and thus, $10^1$ pfu of KGNE-BhKt exhibited a significantly high antitumor effect, rather than $10^7$ pfu of KGΔ-BhKt (p<0.0001). From these results, it was suggested that KGNE-BhKt exhibits an antitumor effect that is at least 1,000,000 times higher than that of KGΔ-BhKt on subcutaneous tumor models of U87 cells.

2-2-5. Comparison Between BhKt Mutation-Introduced Type RR-oHSV and CR-oHSV in Terms of Antitumor Effects Obtained by Systemic Administration In order to examine whether or not KGNE-BhKt exhibits a higher antitumor effect than KGΔ-BhKt even in the case of intravenous administration, KGNE-BhKt or KGΔ-BhKt was intravenously administered to subcutaneous tumor mouse models with U87 cells, and the antitumor effect thereof was then examined. When the volume of a subcutaneous tumor of U87 cells reached approximately 700 mm$^3$, each virus was intravenously administered once (FIG. 14). As a result, in a PBS administration group, the tumor continuously increased in all mice, and in a KGΔ-BhKt administration group, the tumor continuously increased in 4 out of 5 mice. On the other hand, with regard to KGNE-BhKt administration groups, in a $10^7$ pfu KGNE-BhKt administration group, the tumor volume increased until 3 days after the administration, in a $10^6$ pfu KGNE-BhKt administration group, the tumor volume increased until 5 days after the administration, and in a $10^5$ pfu KGNE-BhKt administration group, the tumor volume increased until 7 days after the administration. However, after that, in all of the KGNE-BhKt administration groups, tumor regression started to be observed. In the $10^7$ pfu KGNE-BhKt administration group, the tumors of all of the mice resulted in complete regression by 30 days after the administration, and in the $10^6$ or $10^5$ pfu KGNE-BhKt administration group, the tumors of all of the mice resulted in complete regression by 35 days after the administration. In the KGΔ-BhKt administration group, in the case of one mouse the tumor volume of which was the smallest upon the administration, an increase in the tumor volume was observed until 15 days after the administration, and thereafter, tumor regression was observed. However, during the observation period (for 35 days after the administration of the virus), the tumor volume of the mouse did not become smaller than the tumor volume upon the administration. In all of the mice to which KGNE-BhKt had been administered, the regrowth of the tumor could not be confirmed during the observation period, and no abnormalities were found in the behavioral findings of the mice. The PBS administration group was compared with the KGΔ-BhKt administration group in terms of survival rate. As a result, a significant difference was not found between the two groups (p=0.67). On the other hand, when all of the KGNE-BhKt administration groups were compared with the PBS administration group or the KGΔ-BhKt administration group in terms of survival rate, a significant difference was found (PBS: p=0.0031, KGΔ-BhKt: p=0.014). From these results, it was suggested that KGNE-BhKt exhibits an antitumor effect that is at least 100 times higher than KGΔ-BhKt even under conditions of intravenous administration.

In order to examine whether or not the same results are obtained even in the case of using cancer cell lines other than U87 cells, the antitumor effect of BhKt mutation-introduced type oHSV on subcutaneous tumor models with HepG2 cells was examined. Before in vivo studies, the cell-to-cell spread efficiency and cell-killing ability of each virus on HepG2 cells were examined. As a result, it was suggested that KGNE-BhKt and KGΔ-BhKt have the same level of cell-to-cell spread ability and cell-killing ability (FIG. 15). Moreover, as a result of the introduction of a BhKt mutation into KGNE, the form of a plaque was converted to a plaque form attended with the formation of multinucleated giant cells. However, the cell-to-cell spread efficiency and cell-killing efficiency of KGNE were equivalent to those of KGNE-BhKt (FIG. 15).

In order to compare KGNE-BhKt with KGΔ-BhKt in terms of antitumor effects, when the volume of a subcutaneous tumor of HerpG2 cells transplanted into immunodeficient mice reached approximately 530 mm$^3$, KGΔ-BhKt and KGNE-BhKt were intravenously administered once (FIG. 16). The antitumor effects of individual viruses obtained until 11 days after the administration of the viruses, at which the mice of the PBS administration group reached the endpoint, were compared with the antitumor effects found in the PBS administration group. As a result, in the $10^7$ pfu KGΔ-BhKt administration group and in all of the KGNE-BhKt administration groups, a significantly high antitumor effect was found (p<0.0001). The antitumor effects of KGΔ-BhKt obtained until 28 days after the administration thereof, at which the mice of the KGΔ-BhKt administration group reached the endpoint, were compared with the antitumor effects found in the KGNE-BhKt administration groups. As a result, it was confirmed that the antitumor effects found in all of the KGNE-BhKt administration groups are significantly higher than the antitumor effect found in the KGΔ-BhKt administration group (p<0.0001). From these results, it was suggested that KGNE-BhKt exhibits an antitumor effect that is at least 100 times higher than KGΔ-BhKt even in the HepG2 subcutaneous tumor models.

INDUSTRIAL APPLICABILITY

The virus preparation of the present invention exhibits an extremely high antitumor effect, and thus, utilization thereof in the medical field is expected.

The invention claimed is:

1. A virus preparation for the treatment of a cancer, comprising an HSV (herpes simplex virus) having a receptor-retargeted gD mutation and at least one membrane fusion activity-promoting region on the genome,
wherein the membrane fusion activity-promoting region is a region having a syn mutation, and
wherein the syn mutation is a mutation comprising an amino acid mutation at position 858 of SEQ ID NO: 2 which is a substitution with cysteine or histidine.

2. The virus preparation according to claim 1, wherein the receptor-retargeted gD mutation is a mutation to delete binding ability to nectin-1, the mutation to delete binding ability to nectin-1 being a deletion of all of the amino acids at positions 6 to 38 of SEQ ID NO: 1, a deletion of all of the amino acids at positions 61 to 218 of SEQ ID NO: 1, a mutation of the amino acids at positions 3 and 38 of SEQ ID NO: 1, and/or a mutation of the amino acids at positions 222 and 223 of SEQ ID NO: 1.

3. The virus preparation according to claim 2, wherein the amino acid mutation at position 3 of SEQ ID NO: 1 is a deletion or a substitution with cysteine, the amino acid mutation at position 38 of SEQ ID NO: 1 is a substitution with cysteine, the amino acid mutation at position 222 of SEQ ID NO: 1 is a substitution with asparagine, and the amino acid mutation at position 223 of SEQ ID NO: 1 is a substitution with isoleucine.

4. The virus preparation according to claim 1, wherein the receptor-retargeted gD mutation is a mutation to delete binding ability to HVEM and 3-OS-HS, the mutation to delete binding ability to HVEM and 3-OS-HS being a deletion of all or a part of the amino acids at positions 2 to 38 of SEQ ID NO: 1, a deletion of all of the amino acids at positions 61 to 218 of SEQ ID NO: 1, an amino acid mutation at position 27 of SEQ ID NO: 1, an amino acid mutation at position 29 of SEQ ID NO: 1, and/or an amino acid mutation at position 30 of SEQ ID NO: 1.

5. The virus preparation according to claim 4, wherein: the deletion of a part of the amino acids at positions 2 to 38 of SEQ ID NO: 1 is any of a deletion of the amino acids at positions 2 to 24, a deletion of the amino acids at positions 7 to 11, a deletion of the amino acids at positions 7 to 32, or a deletion of the amino acids at positions 6 to 38; the amino acid mutation at position 27 is a substitution with alanine, proline or arginine; the amino acid mutation at position 29 is a substitution with alanine; and the amino acid mutation at position 30 is a substitution with alanine.

6. The virus preparation according to claim 1, wherein the syn mutation further comprises a mutation described in the following (a), (b), (c) and/or (d):
(a) an amino acid mutation at position 796, an amino acid mutation at position 800, an amino acid mutation at position 813, an amino acid mutation at position 817, an amino acid mutation at position 854, an amino acid mutation at position 855, an insertion of an amino acid between the amino acids at positions 816 and 817, a nonsense mutation in the amino acid at position 877, and/or a nonsense mutation in the amino acid at position 869, of SEQ ID NO: 2;
(b) an amino acid mutation at position 33, an amino acid mutation at position 40, an amino acid mutation at position 86, an amino acid mutation at position 99, an amino acid mutation at position 111, an amino acid mutation at position 121, an amino acid mutation at position 243, an amino acid mutation at position 304, and/or an amino acid mutation at position 310, of SEQ ID NO: 3;
(c) an amino acid mutation at position 49, amino acid mutations at positions 49, 50 and 51, an amino acid mutation at position 209, amino acid mutations at positions 209, 212 and 213, a nonsense mutation in the amino acid at position 217, of SEQ ID NO: 4, and/or a deletion of all of the amino acids shown in SEQ ID NO: 4; and/or
(d) amino acid mutations at position 62, 63 and 64, of SEQ ID NO: 5.

7. The virus preparation according to claim 6, wherein:
the amino acid mutation at position 796 of SEQ ID NO: 2 is a substitution with cysteine, the amino acid mutation at position 800 of SEQ ID NO: 2 is a substitution with tryptophan, the amino acid mutation at position 813 of SEQ ID NO: 2 is a substitution with isoleucine, the amino acid mutation at position 817 of SEQ ID NO: 2 is a substitution with histidine or proline, the amino acid mutation at position 854 of SEQ ID NO: 2 is a substitution with phenylalanine, and the amino acid mutation at position 855 of SEQ ID NO: 2 is a substitution with valine;
the amino acid mutation at position 33 of SEQ ID NO: 3 is a substitution with serine, the amino acid mutation at position 40 of SEQ ID NO: 3 is a substitution with valine or threonine, the amino acid mutation at position 86 of SEQ ID NO: 3 is a substitution with proline, the amino acid mutation at position 99 of SEQ ID NO: 3 is a substitution with asparagine, the amino acid mutation at position 111 of SEQ ID NO: 3 is a substitution with valine, the amino acid mutation at position 121 of SEQ ID NO: 3 is a substitution with isoleucine, the amino acid mutation at position 243 of SEQ ID NO: 3 is a substitution with tyrosine, the amino acid mutation at position 304 of SEQ ID NO: 3 is a substitution with proline, and the amino acid mutation at position 310 of SEQ ID NO: 3 is a substitution with leucine;
the amino acid mutation at position 49 of SEQ ID NO: 4 is a substitution with alanine, the amino acid mutation at position 50 of SEQ ID NO: 4 is a substitution with alanine, the amino acid mutation at position 51 of SEQ ID NO: 4 is a substitution with alanine, the amino acid mutation at position 209 of SEQ ID NO: 4 is a substitution with alanine, the amino acid mutation at position 212 of SEQ ID NO: 4 is a substitution with alanine, and the amino acid mutation at position 213 of SEQ ID NO: 4 is a substitution with alanine; and
the amino acid mutation at position 62 of SEQ ID NO: 5 is a substitution with glycine, the amino acid mutation at position 63 of SEQ ID NO: 5 is a substitution with valine, and the amino acid mutation at position 64 of SEQ ID NO: 5 is a substitution with serine.

8. The virus preparation according to claim 1, wherein a reporter gene and/or a therapeutic gene are incorporated into the genome of the HSV.

9. A therapeutic method for treating a cancer, comprising administering a therapeutically-effective amount of the virus preparation according to claim 1 to a subject in need thereof.

10. A therapeutic method for treating a cancer, comprising administering a therapeutically-effective amount of the virus preparation according to claim 2 to a subject in need thereof.

11. A therapeutic method for treating a cancer, comprising administering a therapeutically-effective amount of the virus preparation according to claim 3 to a subject in need thereof.

12. A therapeutic method for treating a cancer, comprising administering a therapeutically-effective amount of the virus preparation according to claim 4 to a subject in need thereof.

13. A therapeutic method for treating a cancer, comprising administering a therapeutically-effective amount of the virus preparation according to claim 5 to a subject in need thereof.

14. A therapeutic method for treating a cancer, comprising administering a therapeutically-effective amount of the virus preparation according to claim 6 to a subject in need thereof.

15. A therapeutic method for treating a cancer, comprising administering a therapeutically-effective amount of the virus preparation according to claim 7 to a subject in need thereof.

16. A therapeutic method for treating a cancer, comprising administering a therapeutically-effective amount of the virus preparation according to claim 8 to a subject in need thereof.

17. The virus preparation according to claim 1, wherein the receptor-retargeted gD mutation is a deletion of the amino acids at positions 2 to 24 of SEQ ID NO:1 and an amino acid mutation at position 38 of SEQ ID NO:1 which is a substitution with cysteine, wherein the syn mutation further comprises an amino acid mutation at position 40 of SEQ ID NO: 3 which is a substitution with valine or threonine.

18. A therapeutic method for treating a cancer, comprising administering a therapeutically-effective amount of the virus preparation according to claim 17 to a subject in need thereof.

* * * * *

UNITED STATES PATENT AND TRADEMARK OFFICE
CERTIFICATE OF CORRECTION

PATENT NO. : 12,263,197 B2
APPLICATION NO. : 17/288227
DATED : April 1, 2025
INVENTOR(S) : H. Uchida et al.

Page 1 of 1

It is certified that error appears in the above-identified patent and that said Letters Patent is hereby corrected as shown below:

On the Title Page

Foreign Pat. Docs., please add -- WO 03/082200 10/2003 --.

Signed and Sealed this
Twenty-second Day of July, 2025

Coke Morgan Stewart
*Acting Director of the United States Patent and Trademark Office*

SEQUENCE LISTING

<160> NUMBER OF SEQ ID NOS: 7

<210> SEQ ID NO 1
<211> LENGTH: 369
<212> TYPE: PRT
<213> ORGANISM: human herpesvirus 1

<400> SEQUENCE: 1

```
Lys Tyr Ala Leu Ala Asp Ala Ser Leu Lys Met Ala Asp Pro Asn Arg
1               5                  10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
        115                 120                 125

Ile Arg Thr Gln Pro Arg Trp Asn Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255

Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
        275                 280                 285

Gln Ile Pro Pro Asn Trp His Ile Pro Ser Ile Gln Asp Ala Ala Thr
    290                 295                 300

Pro Tyr His Pro Pro Ala Thr Pro Asn Asn Met Gly Leu Ile Ala Gly
305                 310                 315                 320

Ala Val Gly Gly Ser Leu Leu Ala Ala Leu Val Ile Cys Gly Ile Val
                325                 330                 335

Tyr Trp Met His Arg Arg Thr Arg Lys Ala Pro Lys Arg Ile Arg Leu
            340                 345                 350

Pro His Ile Arg Glu Asp Asp Gln Pro Ser Ser His Gln Pro Leu Phe
        355                 360                 365
```

Tyr

<210> SEQ ID NO 2
<211> LENGTH: 904
<212> TYPE: PRT
<213> ORGANISM: human herpesvirus 1

<400> SEQUENCE: 2

```
Met His Gln Gly Ala Pro Ser Trp Gly Arg Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Thr Gln Ala Ala Asn
        35                  40                  45

Gly Gly Pro Ala Thr Pro Ala Pro Pro Ala Leu Gly Ala Ala Pro Thr
    50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300

Glu Gly Ser His Thr Glu His Thr Ser Tyr Ala Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365
```

-continued

```
Trp Gln Glu Val Asp Glu Met Leu Arg Ser Glu Tyr Gly Gly Ser Phe
    370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
                420                 425                 430

His Ile Lys Val Gly Gln Pro Gln Tyr Tyr Leu Ala Asn Gly Gly Phe
            435                 440                 445

Leu Ile Ala Tyr Gln Pro Leu Leu Ser Asn Thr Leu Ala Glu Leu Tyr
450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
                500                 505                 510

Ile Gln Arg His Val Asn Asp Met Leu Gly Arg Val Ala Ile Ala Trp
            515                 520                 525

Cys Glu Leu Gln Asn His Glu Leu Thr Leu Trp Asn Glu Ala Arg Lys
530                 535                 540

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
                580                 585                 590

Pro Gly Ala Cys Tyr Ser Arg Pro Leu Val Ser Phe Arg Tyr Glu Asp
            595                 600                 605

Gln Gly Pro Leu Val Glu Gly Gln Leu Gly Glu Asn Asn Glu Leu Arg
            610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
                660                 665                 670

Leu Asn Ile Thr Met Leu Glu Asp His Glu Phe Val Pro Leu Glu Val
            675                 680                 685

Tyr Thr Arg His Glu Ile Lys Asp Ser Gly Leu Leu Asp Tyr Thr Glu
690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Met Phe Ala Gly Leu Gly
                725                 730                 735

Ala Phe Phe Glu Gly Met Gly Asp Leu Gly Arg Ala Val Gly Lys Val
                740                 745                 750

Val Met Gly Ile Val Gly Gly Val Ser Ala Val Ser Gly Val Ser
            755                 760                 765

Ser Phe Met Ser Asn Pro Phe Gly Ala Leu Ala Val Gly Leu Leu Val
770                 775                 780

Leu Ala Gly Leu Ala Ala Ala Phe Phe Ala Phe Arg Tyr Val Met Arg
```

```
                785                 790                 795                 800
Leu Gln Ser Asn Pro Met Lys Ala Leu Tyr Pro Leu Thr Thr Lys Glu
                    805                 810                 815

Leu Lys Asn Pro Thr Asn Pro Asp Ala Ser Gly Glu Gly Glu Gly
                820                 825                 830

Gly Asp Phe Asp Glu Ala Lys Leu Ala Glu Ala Arg Glu Met Ile Arg
            835                 840                 845

Tyr Met Ala Leu Val Ser Ala Met Glu Arg Thr Glu His Lys Ala Lys
            850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                    885                 890                 895

Gly Asp Ala Asp Glu Asp Leu
                900

<210> SEQ ID NO 3
<211> LENGTH: 338
<212> TYPE: PRT
<213> ORGANISM: human herpesvirus 1

<400> SEQUENCE: 3

Met Leu Ala Val Arg Ser Leu Gln His Leu Ser Thr Val Val Leu Ile
1               5                   10                  15

Thr Ala Tyr Gly Leu Val Leu Val Trp Tyr Thr Val Phe Gly Ala Ser
                20                  25                  30

Pro Leu His Arg Cys Ile Tyr Ala Val Arg Pro Thr Gly Thr Asn Asn
            35                  40                  45

Asp Thr Ala Leu Val Trp Met Lys Met Asn Gln Thr Leu Leu Phe Leu
        50                  55                  60

Gly Ala Pro Thr His Pro Pro Asn Gly Gly Trp Arg Asn His Ala His
65                  70                  75                  80

Ile Cys Tyr Ala Asn Leu Ile Ala Gly Arg Val Val Pro Phe Gln Val
                85                  90                  95

Pro Pro Asp Ala Thr Asn Arg Arg Ile Met Asn Val His Glu Ala Val
            100                 105                 110

Asn Cys Leu Glu Thr Leu Trp Tyr Thr Arg Val Arg Leu Val Val Val
        115                 120                 125

Gly Trp Phe Leu Tyr Leu Ala Phe Val Ala Leu His Gln Arg Arg Cys
130                 135                 140

Met Phe Gly Val Val Ser Pro Ala His Lys Met Val Ala Pro Ala Thr
145                 150                 155                 160

Tyr Leu Leu Asn Tyr Ala Gly Arg Ile Val Ser Ser Val Phe Leu Gln
                165                 170                 175

Tyr Pro Tyr Thr Lys Ile Thr Arg Leu Leu Cys Glu Leu Ser Val Gln
            180                 185                 190

Arg Gln Asn Leu Val Gln Leu Phe Glu Thr Asp Pro Val Thr Phe Leu
        195                 200                 205

Tyr His Arg Pro Ala Ile Gly Val Ile Val Gly Cys Glu Leu Met Leu
    210                 215                 220

Arg Phe Val Ala Val Gly Leu Ile Val Gly Thr Ala Phe Ile Ser Arg
225                 230                 235                 240

Gly Ala Cys Ala Ile Thr Tyr Pro Leu Phe Leu Thr Ile Thr Thr Trp
                245                 250                 255
```

-continued

```
Cys Phe Val Ser Thr Ile Gly Leu Thr Glu Leu Tyr Cys Ile Leu Arg
            260                 265                 270

Arg Gly Pro Ala Pro Lys Asn Ala Asp Lys Ala Ala Ala Pro Gly Arg
            275                 280                 285

Ser Lys Gly Leu Ser Gly Val Cys Gly Arg Cys Cys Ser Ile Ile Leu
            290                 295                 300

Ser Gly Ile Ala Met Arg Leu Cys Tyr Ile Ala Val Val Ala Gly Val
305                 310                 315                 320

Val Leu Val Ala Leu His Tyr Glu Gln Glu Ile Gln Arg Arg Leu Phe
            325                 330                 335

Asp Val

<210> SEQ ID NO 4
<211> LENGTH: 222
<212> TYPE: PRT
<213> ORGANISM: human herpesvirus 1

<400> SEQUENCE: 4

Met Thr Met Arg Asp Asp Leu Pro Leu Val Asp Arg Asp Leu Val Asp
1               5                   10                  15

Glu Ala Ala Phe Gly Gly Glu Gly Glu Leu Pro Leu Glu Glu Gln
            20                  25                  30

Phe Ser Leu Ser Ser Tyr Gly Thr Ser Asp Phe Phe Val Ser Ser Ala
            35                  40                  45

Tyr Ser Arg Leu Pro Pro His Thr Gln Pro Val Phe Ser Lys Arg Val
            50                  55                  60

Ile Leu Phe Leu Trp Ser Phe Leu Val Leu Lys Pro Leu Glu Met Val
65                  70                  75                  80

Ala Ala Gly Met Tyr Tyr Gly Leu Thr Gly Arg Val Val Ala Pro Ala
            85                  90                  95

Cys Ile Leu Ala Ala Ile Val Gly Tyr Tyr Val Thr Trp Ala Val Arg
            100                 105                 110

Ala Leu Leu Leu Tyr Val Asn Ile Lys Arg Asp Arg Leu Pro Leu Ser
            115                 120                 125

Ala Pro Val Phe Trp Gly Met Ser Val Phe Leu Gly Gly Thr Ala Leu
            130                 135                 140

Cys Ala Leu Phe Ala Ala Ala His Glu Thr Phe Ser Pro Asp Gly Leu
145                 150                 155                 160

Phe His Phe Ile Ala Thr Asn Gln Met Leu Pro Pro Thr Asp Pro Leu
            165                 170                 175

Arg Thr Arg Ala Leu Gly Ile Ala Cys Ala Gly Ala Ser Met Trp
            180                 185                 190

Val Ala Ala Ala Asp Ser Phe Ala Ala Ser Ala Asn Phe Phe Leu Ala
            195                 200                 205

Arg Phe Trp Thr Arg Ala Ile Leu Asn Ala Pro Val Ala Phe
            210                 215                 220

<210> SEQ ID NO 5
<211> LENGTH: 269
<212> TYPE: PRT
<213> ORGANISM: human herpesvirus 1

<400> SEQUENCE: 5

Met Ala Ala Arg Thr Arg Ser Leu Val Glu Arg Arg Val Leu Met
1               5                   10                  15

Ala Gly Val Arg Ser His Thr Arg Phe Tyr Lys Ala Leu Ala Lys Glu
```

```
            20                  25                  30
Val Arg Glu Phe His Ala Thr Lys Ile Cys Gly Thr Leu Leu Thr Leu
        35                  40                  45

Leu Ser Gly Ser Leu Gln Gly Arg Ser Val Phe Glu Ala Thr Arg Val
    50                  55                  60

Thr Leu Ile Cys Glu Val Asp Leu Gly Pro Arg Pro Asp Cys Ile
65                  70                  75                  80

Cys Val Phe Glu Phe Ala Asn Asp Lys Thr Leu Gly Gly Val Cys Val
                85                  90                  95

Ile Ile Glu Leu Lys Thr Cys Lys Tyr Ile Ser Ser Gly Asp Thr Ala
            100                 105                 110

Ser Lys Arg Glu Gln Arg Ala Thr Gly Met Lys Gln Leu Arg His Ser
        115                 120                 125

Leu Lys Leu Leu Gln Ser Leu Ala Pro Pro Gly Asp Lys Ile Val Tyr
    130                 135                 140

Leu Cys Pro Val Leu Val Phe Val Ala Gln Arg Thr Leu Arg Val Ser
145                 150                 155                 160

Arg Val Thr Arg Leu Val Pro Gln Lys Val Ser Gly Asn Ile Thr Ala
                165                 170                 175

Val Val Arg Met Leu Gln Ser Leu Ser Thr Tyr Thr Val Pro Met Glu
            180                 185                 190

Pro Arg Thr Gln Arg Ala Arg Arg Arg Gly Gly Ala Ala Arg Gly
        195                 200                 205

Ser Ala Ser Arg Pro Lys Arg Ser His Ser Gly Ala Arg Asp Pro Pro
    210                 215                 220

Glu Pro Ala Ala Arg Gln Val Pro Pro Ala Asp Gln Thr Pro Ala Ser
225                 230                 235                 240

Thr Glu Gly Gly Gly Val Leu Lys Arg Ile Ala Ala Leu Phe Cys Val
                245                 250                 255

Pro Val Ala Thr Lys Thr Lys Pro Arg Ala Ala Ser Glu
            260                 265

<210> SEQ ID NO 6
<211> LENGTH: 72
<212> TYPE: DNA
<213> ORGANISM: Artificial Sequence
<220> FEATURE:
<223> OTHER INFORMATION: Synthetic primer

<400> SEQUENCE: 6
cccaggtaac ctccacgccc aactcggaac ccgtggtcag gagcgcgccc aggatgacga      60
cgataagtag gg                                                         72

<210> SEQ ID NO 7
<211> LENGTH: 128
<212> TYPE: DNA
<213> ORGANISM: Artificial Sequence
<220> FEATURE:
<223> OTHER INFORMATION: Synthetic primer

<400> SEQUENCE: 7
gacgactcgg cggacgctgg ttggccgggc ccgccgcgc tggcggccgc gggcgcgctc       60
ctgaccacgg gttccgagtt gggcgtggag gttacctggg ctacaaccaa ttaaccaatt    120
ctgattag                                                            128
```